(12) United States Patent
Ni et al.

(10) Patent No.: US 7,803,615 B1
(45) Date of Patent: *Sep. 28, 2010

(54) DEATH DOMAIN CONTAINING RECEPTOR 5

(75) Inventors: Jian Ni, Rockville, MD (US); Reiner L. Gentz, Silver Spring, MD (US); Guo-Liang Yu, Darnestown, MD (US); Jeffrey Y. Su, Gaithersburg, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 1248 days.

This patent is subject to a terminal disclaimer.

(21) Appl. No.: 09/042,583

(22) Filed: Mar. 17, 1998

Related U.S. Application Data

(60) Provisional application No. 60/040,846, filed on Mar. 17, 1997, provisional application No. 60/054,021, filed on Jul. 29, 1997.

(51) Int. Cl.
*C07K 14/705* (2006.01)
*C12N 5/10* (2006.01)
*C12N 15/12* (2006.01)
*C12N 15/62* (2006.01)
*C12N 15/63* (2006.01)

(52) U.S. Cl. ............... 435/325; 536/23.4; 536/23.5; 536/23.53; 435/69.1; 435/69.7; 435/252.3; 435/254.11; 435/320.1

(58) Field of Classification Search ............... 536/23.1, 536/23.5, 23.4, 24.3; 435/69.1, 69.7, 320.1, 435/325, 252.3, 254.11; 530/350, 300; 424/184.1, 424/185.1; 436/96.7
See application file for complete search history.

(56) References Cited

U.S. PATENT DOCUMENTS

| | | | |
|---|---|---|---|
| 5,763,223 A * | 6/1998 | Wiley et al. | |
| 6,072,047 A | 6/2000 | Rauch et al. | |
| 6,313,269 B1 | 11/2001 | Deen et al. | |
| 6,342,363 B1 | 1/2002 | Ni et al. | |
| 6,342,369 B1 | 1/2002 | Ashkenazi | |
| 6,433,147 B1 | 8/2002 | Ni et al. | |
| 6,461,823 B1 | 10/2002 | Ni et al. | |
| 6,569,642 B1 | 5/2003 | Rauch et al. | |
| 6,743,625 B2 | 6/2004 | Ni et al. | |
| 2002/0048785 A1 | 4/2002 | Holtzman | |
| 2002/0098550 A1 | 7/2002 | Ni et al. | |
| 2002/0160446 A1 | 10/2002 | Holtzman et al. | |
| 2003/0125540 A1 | 7/2003 | Holtzman et al. | |
| 2006/0115484 A1* | 6/2006 | Adams et al. | |

FOREIGN PATENT DOCUMENTS

| | | |
|---|---|---|
| EP | 0510691 | 10/1992 |
| EP | 0 870 827 A2 | 10/1998 |
| EP | 0 870 827 A3 | 10/1998 |
| EP | 1 181 319 A0 | 12/2000 |
| EP | 1 192 185 A0 | 12/2000 |
| EP | 1 287 035 A1 | 3/2003 |
| WO | WO 91/09967 * | 7/1991 |
| WO | WO 94/01548 * | 1/1994 |
| WO | WO 98/32856 A1 | 7/1998 |
| WO | WO 98/35986 | 8/1998 |
| WO | WO 98/41629 A2 | 9/1998 |
| WO | WO 98/41629 A3 | 9/1998 |
| WO | WO 98/46643 A1 | 10/1998 |
| WO | WO 98/51793 A1 | 11/1998 |
| WO | WO 98/58062 A1 | 12/1998 |
| WO | WO 99/00423 A1 | 1/1999 |

OTHER PUBLICATIONS

GenBank Accession No. Z66083, H. Sapiens CpG island DNA genomic MseI fragment, clone 75a7, reverse read cpg75a7.rtla, accessed Dec. 1998, Oct. 23, 1995.*
Bjorn et al., Fusion proteins in biotechnology and structural biology, Current Biol., 2: 569-575, 1992.*
Stratagene Clonging Systems catalog, p. 304, 1994.*
Smith et al., The TNF receptor superfamily of cellular and viral proteins; activation, costimulation and death, Cell 76:959-962, Mar. 25, 1994.*
Pan, G. et al., Science 277: 815-818 (Aug. 1997).
Sheridan, J. P., et al., Science 277: 818-821 (Aug. 1997).
Pan, G. et al., Science 276: 111-113 (Apr. 1997).
Chinnaiyan, A. M., et al., Science 274: 990-992 (Nov. 1996).
GenBank Accesion No. AA223122 Feb. 19, 1997.
GenBank Accesion No. AA232440 Feb. 28, 1997.
Beutler, B., and Cerami, A., "Tumor Necrosis, Cachexia, Shock, and Inflammation: A Common Mediator," *Ann. Rev. Biochem.* 57:505-518, Annual Reviews Inc. (1988).
Fiers, W., "Tumor necrosis factor. Characterization at the molecular, cellular and in vivo level," *FEBS Lett.* 285:199-212, Elsevier Science B.V. (1991).
Goeddel, D.V., et al., "Tumor Necrosis Factors: Gene Structure and Biological Activities," *Cold Spring Harb. Symp. Quant. Biol. 51 (Pt. 1)*:597-609, Cold Spring Harbor Laboratory Press (1986).
Golstein, P., "Cell death: TRAIL and its receptors," *Curr. Biol.* 7:R750-R753, Current Biology Ltd. (Dec. 1997).
Gruss, H.-J., and Dower, S.K., "Tumor Necrosis Factor Ligand Superfamily: Involvement in the Pathology of Malignant Lymphomas," *Blood 85*:3378-3404, The American Society of Hematology (1995).
Locksley, R.M., et al., "The TNF and TNF Receptor Superfamilies: Integrating Mammalian Biology," *Cell 104*:487-501, Cell Press (Feb. 2001).
Nagata, S., "Apoptosis by Death Factor," *Cell 88*:355-365, Cell Press (Feb. 1997).
Old, L.J., "Tumor Necrosis Factor," *Scientific American*, pp. 59-75, Scientific American, Inc. (May 1988).

(Continued)

*Primary Examiner*—Gary B. Nickol
*Assistant Examiner*—Claire Kaufman

(57) ABSTRACT

The present invention relates to novel Death Domain Containing Receptor-5 (DR5) proteins which are members of the tumor necrosis factor (TNF) receptor family, and have now been shown to bind TRAIL. In particular, isolated nucleic acid molecules are provided encoding the human DR5 proteins. DR5 polypeptides are also provided as are vectors, host cells and recombinant methods for producing the same. The invention further relates to screening methods for identifying antagonists and antagonists of DR5 activity.

50 Claims, 12 Drawing Sheets

OTHER PUBLICATIONS

Wallach, D., "TNF Ligand and TNF/NGF Receptor Families," in *Cytokine Reference. A compendium of cytokines and other mediators of host defense*, Oppenheim, J.J., et al., eds., Academic Press, Inc., San Diego, CA, pp. 377-411 (Aug. 2000).

Allison, J., et al., "Transgenic expression of CD95 ligand on islet β cells induces a granulocytic infiltration but does not confer immune privilege upon islet allografts," *Proc. Natl. Acad. Sci. USA 94*:3943-3947, National Academy Press (Apr. 1997).

Allison, J., and Strasser, A., "Mechanisms of β cell death in diabetes: A minor role for CD95," *Proc. Natl. Acad. Sci. USA 95*:13818-13822, National Academy Press (Nov. 1998).

Bodmer, J.-L., et al., "TRAMP, a Novel Apoptosis-Mediating Receptor with Sequence Homology to Tumor Necrosis Factor Receptor 1 and Fas(Apo-1/CD95)," *Immunity 6*:79-88, Cell Press (Jan. 1997).

Boldin, M.P., et al., "A Novel Protein That Interacts with the Death Domain of Fas/APO1 Contains a Sequence Motif Related to the Death Domain," *J. Biol. Chem. 270*:7795-7798, American Society for Biochemistry and Molecular Biology, Inc. (1995).

Chicheportiche, Y., et al., "TWEAK, a New Secreted Ligand in the Tumor Necrosis Factor Family That Weakly Induces Apoptosis," *J. Biol. Chem. 272*:32401-32410, American Society for Biochemistry and Molecular Biology, Inc. (Dec. 1997).

Chinnaiyan, A.M., et al., "FADD, a Novel Death Domain-Containing Protein, Interacts with the Death Domain of Fas and Initiates Apoptosis," *Cell 81*:505-512, Cell Press (1995).

Clerici, M., et al., "Type 1 and Type 2 Cytokines in HIV Infection—A Possible Role in Apoptosis and Disease Progression," *Ann. Med. 29*:185-188, Finnish Medical Society DUODECIM (Jun. 1997).

Degli-Esposti, M.A., et al., "Cloning and Characterization of TRAIL-R3, a Novel Member of the Emerging TRAIL Receptor Family," *J. Exp. Med. 186*:1165-11170, Rockefeller University Press (Oct. 1997).

Degli-Esposti, M.A., et al., "The Novel Receptor TRAIL-R4 Induces NF-κB and Protects against TRAIL-Mediated Apoptosis, yet Retains an Incomplete Death Domain," *Immunity 7*:813-820, Cell Press (Dec. 1997).

Duan, H. and Dixit, V.M., "RAIDD is a new 'death' adaptor molecule," *Nature 385*:86-89, Macmillan Publishers, Ltd. (Jan. 1997).

Frankfurt, O.S., et al., "Protection from Apoptotic Cell Death by Interleukin-4 is Increased in Previously Treated Chronic Lymphocytic Leukemia Patients," *Leuk. Res. 21*:9-16, Elsevier Science, Ltd (Jan. 1997).

Gooch, J.L., et al., "Interleukin 4 Inhibits Growth and Induces Apoptosis in Human Breast Cancer Cells," *Cancer Res. 58*:4199-4205, American Association for Cancer Research (Sep. 1998).

Grell, M., et al., "Induction of cell death by tumour necrosis factor (TNF) receptor 2, CD40 and CD30: a role for TNF-R1 activation by endogenous membrane-anchored TNF," *EMBO J. 18*:3034-3043, Oxford University Press (Jun. 1999).

Hardiman, G., et al., "Genetic Structure and Chromosomal Mapping of MyD88," *Genomics 45*:332-339, Academic Press (Oct. 1997).

Hildeman, D.A., et al., "Activated T Cell Death in Vivo Mediated by Proapoptotic Bcl-2 Family Member Bim," *Immunity 16*:759-767, Cell Press (Jun. 2002).

Hill, M.E., et al., "Prognostic Significance of BCL-2 Expression and *bcl-2* Major Breakpoint Region Rearrangement in Diffuse Large Cell Non-Hodgkin's Lymphoma: A British National Lymphoma Investigation Study," *Blood 88*:1046-105, American Society of Hematology (Aug. 1996).

Hofmann, K., and Bucher, P., "The CARD domain: a new apoptotic signalling motif," *Trends Biochem. Sci. 22*:155-156, Elsevier Science, Ltd. (May 1997).

Horigome, A., et al., "Tacrolimus-induced apoptosis and its prevention by interleukins in mitogen-activated human peripheral-blood mononuclear cells," *Immunopharmacology 39*:21-30, Elsevier Science B.V. (Mar. 1998).

Hsu, H., et al., "TRADD-TRAF2 and TRADD-FADD Interactions Define Two Distinct TNF Receptor 1 Signal Transduction Pathways," *Cell 84*:299-308, Cell Press (Jan. 1996).

Huang, D.C.S., et al., "Activation of Fas by FasL induces apoptosis by a mechanism that cannot be blocked by Bcl-2 or Bcl-$x_L$," *Proc. Natl. Acad. Sci. USA 96*:14871-14876, National Academy Press (Dec. 1999).

Huang, D.C.S., et al., "Bcl-2, Bcl-$x_L$ and adenovirus protein E1B19kD are functionally equivalent in their ability to inhibit cell death," *Oncogene 14*:405-414, Stockton Press (Jan. 1997).

Irmler, M., et al., "Direct physical interaction between the *Caenorhabditis elegans* 'death proteins' CED-3 and CED-4," *FEBS Lett. 406*:189-190, Elsevier Science B.V. (Apr. 1997).

Irmler, M., et al., "Inhibition of death receptor signals by cellular FLIP," *Nature 388*:190-195, Macmillan Publishers, Ltd. (Jul. 1997).

Karin, M., and Lin, A., "NF-κB at the crossroads of life and death," *Nat. Immunol. 3*:221-227, Nature Publishing Group (Mar. 2002).

Kelliher, M.A., et al., "The Death Domain Kinase RIP Mediates the TNF-Induced NF-κB Signal," *Immunity 8*:297-303, Cell Press (Mar. 1998).

Lindner, H., et al., "Peripheral Blood Mononuclear Cells Induce Programmed Cell Death in Human Endothelial Cells and May Prevent Repair: Role of Cytokines," *Blood 89*:1931-1938, American Society of Hematology (Mar. 1997).

Lotem, J., and Sachs, L., "Hematopoietic Cytokines Inhibit Apoptosis Induced by Transforming Growth Factor β1 and Cancer Chemotherapy Compounds in Myeloid Leukemic Cells," *Blood 80*:1750-1757, American Society of Hematology (1992).

Lotem, J., and Sachs, L., "Interferon-γ inhibits apoptosis induced by wild-type p53, cytotoxic anti-cancer agents and viability factor deprivation in myeloid cells," *Leukemia 9*:685-692, Stockton Press (1995).

MacFarlane, M., et al., "Identification and Molecular Cloning of Two Novel Receptors for the Cytotoxic Ligand TRAIL," *J. Biol. Chem. 272*:25417-25420, American Society for Biochemistry and Molecular Biology, Inc. (Oct. 1997).

Muzio, M., et al., "FLICE, a Novel FADD-Homologous ICE/CED-3-like Protease, Is Recruited to the CD95 (Fas/APO-1) Death-Inducing Signaling Complex," *Cell 85*:817-827, Cell Press (Jun. 1996).

Muzio, M., et al., "IRAK (Pelle) Family Member IRAK-2 and MyD88 as Proximal Mediators of IL-1 Signaling," *Science 278*:1612-1615, American Association for the Advancement of Science (Nov. 1997).

Newton, K., et al., "A dominant interfering mutant of FADD/MORT1 enhances deletion of autoreactive thymocytes and inhibits proliferation of mature T lymphocytes," *EMBO J. 17*:706-718, Oxford Univeristy Press (Feb. 1998).

Newton, K., et al., "FADD/MORT1 regulates the pre-TCR checkpoint and can function as a tumour suppressor," *EMBO J. 19*:931-941, Oxford University Press (Mar. 2000).

Newton, K., et al., "Effects of a dominant interfering mutant of FADD on signal transduction in activated T cells," *Curr. Biol. 11*:273-276, Elsevier Science, Ltd. (Feb. 2001).

Newton, K., and Strasser, A., "Ionizing Radiation and Chemotherapeutic Drugs Induce Apoptosis in Lymphocytes in the Absence of Fas or FACC/MORT1 Signaling: Implications for Cancer Therapy," *J. Exp. Med. 191*:195-200, Rockefeller University Press (Jan. 2000).

O'Conner, L., and Strasser, A., "Fas, p53, and Apoptosis," *Science 284*:1431b, American Association for the Advancement of Science (May 1999).

O'Conner, L., et al., "CD95 (Fas/APO-1) and p53 Signal Apoptosis Independently in Diverse Cell Types," *Cancer Res. 60*:1217-1220, American Association for Cancer Research (Mar. 2000).

Odaka, C., et al., "Immunosuppressant deoxyspergualin induces apoptotic cell death in dividing cells," *Immunol. 95*:370-376, Blackwell Science, Ltd. (Nov. 1998).

Pan, G., et al., "TRUNDD, a new member of the TRAIL receptor family that antagonizes TRAIL signalling," *FEBS Lett. 424*:41-45, Elsevier Science B.V. (Mar. 1998).

Screaton, G.R., et al., "LARD: A new lymphoid-specific death domain containing receptor regulated by alternative pre-mRNA splicing," *Proc. Natl. Acad. Sci. USA 94*:4615-4619, National Academy Press (Apr. 1997).

Simonitsch, I., and Krupitza, G., "Autocrine self-elimination of cultured ovarian cancer cells by tumour necrosis factor α (TNF-α)," *Br. J. Cancer* 78:862-870, Nature Publishing Group on behalf of Cancer Research, UK (Oct. 1998).

Smith, K.G.C., et al., "CrmA expression in T lymphocytes of transgenic mice inhibits CD95 (Fas/APO-1)-transduced apoptosis, but does not cause lymphodenopathy or autoimmune disease," *EMBO J.* 15:5167-5176, Oxford University Press (Oct. 1996).

Strasser, A., et al., "Bcl-2 and Fas/APO-1 regulate distinct pathways to lymphocyte apoptosis," *EMBO J.* 14:6136-1647, Oxford University Press (1995).

Thome, M., et al., "Viral FLICE-inhibitory proteins (FLIPs) prevent apoptosis induced by death receptors," *Nature* 386:517-521, Macmillan Publishers, Ltd. (Apr. 1997).

Villunger, A., et al., "Fas Ligand, Bcl-2, Granulocyte Colony-Stimulating Factor, and p38 Mitogen-activated Protein Kinase: Regulators of Distinct Cell Death and Survival Pathways in Granulocytes," *J. Exp. Med.* 192:647-657, Rockefeller University Press (Sep. 2000).

Villunger, A., et al., "Fas Ligand-Induced c-Jun Kinase Activation in Lymphoid Cells Requires Extensive Receptor Aggregation But Is Independent of DAXX, and Fas-Mediated Cell Death Does Not Involve DAXX, RIP, or RAIDD," *J. Immunol.* 165:1337-1343, American Association of Immunologists (Aug. 2000).

Walczak, H., et al., "TRAIL-R2: a novel apoptosis-mediating receptor for TRAIL," *EMBO J.* 16:5386-5397, Oxford University Press (Sep. 1997).

Watanabe-Fukunaga, R., et al., "Lymphoproliferation disorder in mice explained by defects in Fas antigen that mediates apoptosis," *Nature* 356:314-317, Macmillan Publishers, Ltd. (1992).

Wong, B.B., et al., "TRANCE Is a Novel Ligand of the Tumor Necrosis Factor Receptor Family That Activates c-Jun N-terminal Kinase in T Cells," *J. Biol. Chem.* 272:25190-25194, American Society for Biochemistry and Molecular Biology, Inc. (Oct. 1997).

Yoshida, T., et al., "Rapid B cell apoptosis induced by antigen receptor ligation does not require Fas (CD95/APO-1), the adaptor protein FADD/MORT1 or CrmA-sensitive caspases but is defective in both MRL-+/+ and MRL-*lpr*/lpr mice," *Int. Immunol.* 12:517-526, Japanese Society for Immunology (Apr. 2000).

Zou, W., et al., "Administration of Interleukin 13 to Simian Immunodeficiency Virus-Infected Macaques: Induction of Intestinal Epithelial Atrophy," *AIDS Res Hum Retroviruses* 14:775-793, Mary Ann Liebert, Inc. (Jun. 1998).

European Search Report for European Application No. EP 00 93 0329 mailed on Feb. 6, 2004, Munich, Germany.

Co-Pending U.S. Appl. No. 09/565,009, Ni et al., filed May 4, 2000.

Co-Pending U.S. Appl. No. 10/005,842, Ni et al., filed Dec. 7, 2001, now U.S. Published Patent Application No. 2002/0098550 (Document AD1).

Co-Pending U.S. Appl. No. 10/648,825, Ni et al., filed Aug. 27, 2003, now US Published Patent Application No. 2004/0136951.

Co-Pending U.S. Appl. No. 10/774,622, Ni et al., filed Feb. 10, 2004, now US Published Patent Application No. 2004/0141952.

Australian Opposition Document, Evidence in Support: Statutory Declaration of Andreas Strasser dated Apr. 7, 2005 together with Exhibits AS-10 to AS-23, submitted by Genentech, Inc. in the Opposition to Australian Patent Application 747635 (67635/98), 467 pages.

Brojatsch, J., et al., "CAR1, a TNFR-Related Protein, Is a Cellular Receptor for Cytopathic Avian Leukosis-Sarcoma Viruses and Mediates Apoptosis," *Cell* 87:845-855, Cell Press (Nov. 1996).

Chapman, B.S., "A region of the 75 kDa neurotrophin receptor homologous to the death domains of TNFR-i and Fas," *FEBS Lett.* 374:216-220, Elsevier (1995).

Rabizadeh, S., et al., "Induction of Apoptosis by the Low-Affinity NGF Receptor," *Science* 261:345-348, American Association for the Advancement of Science (1993).

Tartaglia, L.A., et al., "A Novel Domain within the 55 kd TNF Receptor Signals Cell Death," *Cell* 74:845-853, Cell Press (1993).

Statutory Declaration of Avi J. Ashkenazi, signed Mar. 14, 2003.

Curriculum vitae of Avi Ashkenazi, Mar. 2003.

U.S. Appl. No. 60/040,846, inventor Ni et al., filed Mar. 17, 1997.

U.S. Appl. No. 60/054,021, inventor Ni et al., filed Jul. 29. 1997.

U.S. Appl. No. 08/857,216, inventor Ashkenazi, filed May 15, 1997.

Chaudhary, P.M. et al., "Death Receptor 5, a New Member of the TNFR Family, and DR4 Induce FADD-Dependent Apoptosis and Active the NF-κB Pathway," *Immunity* 7:821-830 (Dec. 1997).

Marsters, S.A. et al., "A novel receptor for APO2L/TRAIL contains a truncated death domain," *Curr. Biol.* 7:1003-1006 (Dec. 1997).

Rieger, J. et al., "APO2 ligand: a novel lethal weapon against malignant glioma?" *FEBS Lett.* 427:124-128 (May 1998).

Schneider, P. et al., "TRAIL Receptors 1 (DR4) and 2 (DR5) Signal FADD-Dependent Apoptosis and Activate NF-κB," *Immunity* 7:831-836 (Dec. 1997).

Sheikh, S.M. et al., "p53-dependent and—independent Regulation of the Death Receptor *KILLER/DR5* Gene Expression in Response to Genotoxic Stress and Tumor Necrosis Factor α," *Cancer Res.* 58:1593-1598 (Apr. 1998).

Zamai, et al., "Natural killer (NK) Cell-mediated Cytotoxicity: Differential Use of TRAIL and Fas Ligand by Immature and Mature Primary Human NK Cells," *J. Exp. Med.* 188:2375-2380 (Dec. 1998).

* cited by examiner

```
                    10                    30                    50
         CACGCGTCCGCGGGCGCGGCCGGAGAACCCCGCAATCTTTGCGCCCACAAAATACACCGA
                    70                    90                   110
         CGATGCCCGATCTACTTTAAGGGCTGAAACCCACGGGCCTGAGAGACTATAAGAGCGTTC
                   130                   150                   170
         CCTACCGCCATGGAACAACGGGGACAGAACGCCCCGGCCGCTTCGGGGGCCCGGAAAAGG
                    M   E   Q   R   G   Q   N   A   P   A   A   S   G   A   R   K   R
                   190                   210                   230
         CACGGCCCAGGACCCAGGGAGGCGCGGGGAGCCAGGCCTGGGCCCCGGGTCCCCAAGACC
          H   G   P   G   P   R   E   A   R   G   A   R   P   G   P   R   V   P   K   T
                   250                   270                   290
         CTTGTGCTCGTTGTCGCCGCGGTCCTGCTGTTGGTCTCAGCTGAGTCTGCTCTGATCACC
          L   V   L   V   V   A   A   V   L   L   L   V   S   A   E   S   A   L   I   T
                   310                   330                   350
         CAACAAGACCTAGCTCCCCAGCAGAGAGCGGCCCCACAACAAAAGAGGTCCAGCCCCTCA
          Q   Q   D   L   A   P   Q   Q   R   A   A   P   Q   Q   K   R   S   S   P   S
                   370                   390                   410
         GAGGGATTGTGTCCACCTGGACACCATATCTCAGAAGACGGTAGAGATTGCATCTCCTGC
          E   G   L   C   P   P   G   H   H   I   S   E   D   G   R   D   C   I   S   C
                   430                   450                   470
         AAATATGGACAGGACTATAGCACTCACTGGAATGACCTCCTTTTCTGCTTGCGCTGCACC
          K   Y   G   Q   D   Y   S   T   H   W   N   D   L   L   F   C   L   R   C   T
                   490                   510                   530
         AGGTGTGATTCAGGTGAAGTGGAGCTAAGTCCCTGCACCACGACCAGAAACACAGTGTGT
          R   C   D   S   G   E   V   E   L   S   P   C   T   T   T   R   N   T   V   C
                   550                   570                   590
         CAGTGCGAAGAAGGCACCTTCCGGGAAGAAGATTCTCCTGAGATGTGCCGGAAGTGCCGC
          Q   C   E   E   G   T   F   R   E   E   D   S   P   E   M   C   R   K   C   R
                   610                   630                   650
         ACAGGGTGTCCCAGAGGGATGGTCAAGGTCGGTGATTGTACACCCTGGAGTGACATCGAA
          T   G   C   P   R   G   M   V   K   V   G   D   C   T   P   W   S   D   I   E
                   670                   690                   710
         TGTGTCCACAAAGAATCAGGCATCATCATAGGAGTCACAGTTGCAGCCGTAGTCTTGATT
          C   V   H   K   E   S   G   I   I   I   G   V   T   V   A   A   V   V   L   I
                   730                   750                   770
         GTGGCTGTGTTTGTTTGCAAGTCTTTACTGTGGAAGAAAGTCCTTCCTTACCTGAAAGGC
          V   A   V   F   V   C   K   S   L   L   W   K   K   V   L   P   Y   L   K   G
                   790                   810                   830
         ATCTGCTCAGGTGGTGGTGGGGACCCTGAGCGTGTGGACAGAAGCTCACAACGACCTGGG
          I   C   S   G   G   G   G   D   P   E   R   V   D   R   S   S   Q   R   P   G
```

FIG.1A

```
                850                       870                       890
GCTGAGGACAATGTCCTCAATGAGATCGTGAGTATCTTGCAGCCCACCCAGGTCCCTGAG
 A  E  D  N  V  L  N  E  I  V  S  I  L  Q  P  T  Q  V  P  E
                910                       930                       950
CAGGAAATGGAAGTCCAGGAGCCAGCAGAGCCAACAGGTGTCAACATGTTGTCCCCCGGG
 Q  E  M  E  V  Q  E  P  A  E  P  T  G  V  N  M  L  S  P  G
                970                       990                      1010
GAGTCAGAGCATCTGCTGGAACCGGCAGAAGCTGAAAGGTCTCAGAGGAGGAGGCTGCTG
 E  S  E  H  L  L  E  P  A  E  A  E  R  S  Q  R  R  R  L  L
               1030                      1050                      1070
GTTCCAGCAAATGAAGGTGATCCCACTGAGACTCTGAGACAGTGCTTCGATGACTTTGCA
 V  P  A  N  E  G  D  P  T  E  T  L  R  Q  C  F  D  D  F  A
               1090                      1110                      1130
GACTTGGTGCCCTTTGACTCCTGGGAGCCGCTCATGAGGAAGTTGGGCCTCATGGACAAT
 D  L  V  P  F  D  S  W  E  P  L  M  R  K  L  G  L  M  D  N
               1150                      1170                      1190
GAGATAAAGGTGGCTAAAGCTGAGGCAGCGGGCCACAGGGACACCTTGTACACGATGCTG
 E  I  K  V  A  K  A  E  A  A  G  H  R  D  T  L  Y  T  M  L
               1210                      1230                      1250
ATAAAGTGGGTCAACAAAACCGGGCGAGATGCCTCTGTCCACACCCTGCTGGATGCCTTG
 I  K  W  V  N  K  T  G  R  D  A  S  V  H  T  L  L  D  A  L
               1270                      1290                      1310
GAGACGCTGGGAGAGAGACTTGCCAAGCAGAAGATTGAGGACCACTTGTTGAGCTCTGGA
 E  T  L  G  E  R  L  A  K  Q  K  I  E  D  H  L  L  S  S  G
               1330                      1350                      1370
AAGTTCATGTATCTAGAAGGTAATGCAGACTCTGCCATGTCCTAAGTGTGATTCTCTTCA
 K  F  M  Y  L  E  G  N  A  D  S  A  M  S  *
               1390                      1410                      1430
GGAAGTGAGACCTTCCCTGGTTTACCTTTTTTCTGGAAAAAGCCCAACTGGACTCCAGTC
               1450                      1470                      1490
AGTAGGAAAGTGCCACAATTGTCACATGACCGGTACTGGAAGAAACTCTCCCATCCAACA
               1510                      1530                      1550
TCACCCAGTGGATGGAACATCCTGTAACTTTTCACTGCACTTGGCATTATTTTTATAAGC
               1570                      1590
TGAATGTGATAATAAGGACACTATGGAAAAAAAAAAAAA
```

```
241 TLSQV------KGFVRKNGVNEAKIDEIKNDNVQDTA   h Fas protein
358 TLYAVVENVPPLRWKEFVRRLGLSDHEIDRLELQNGRCLR  h TNFR I Protein
335 -LYDVMDAVPARRWKEFVRTLGLREAEIEAVEVEIGR-FR  DR3 protein
312 CFDDFADLVPFDSWEPLMRKLGLMDNEI-KVAKAEAAGHR  HLYBX88XXprotein 272 EQKVQLLRNWHQLHGKKEA-YDTLIKDLKKANLCTLAEKI  h Fas protein
398 EAQYSMLATWRRTPRREATLELLGRVLRDMDLLGCLEDIH  h TNFR I Protein
373 DQQYEMLKRWRQQP--AGLGAVYAALERMGLDGCVEDL    DR3 protein
351 DTLYTMLIKWVNKTGR-DASVHTLLDALETLGERLAKQKI  HLYBX88XXprotein 311 QTIILKDITSDSENSNFRNEIQSLV                 h Fas protein
438 EEAL---CGPAALPPAPSLLR                     h TNFR I Protein
410 ------RSRLQRGP                            DR3 protein
390 EDHLLSSGKFMYLEGN--ADSAMS                  HLYBX88XXprotein
```

FIG.2C

HAPBU13R
    1 AATTCGGCAC AGCTCTTCAG GAAGTCAGAC CTTCCCTGGT TTACCTTTTT
   51 TCTGGAAAAA GCCCAACTGG GACTCCAGTC AGTAGGAAAG TGCCACAATT
  101 GTCACATGAC CGGTACTGGA AGAAACTCTC CCATCCAACA TCACCCAGTG
  151 GNATGGGAAC ACTGATGAAC TTTTCACTGC ACTTGGCATT ATTTTTGTNA
  201 AGCTGAATGT GATAATAAGG GCACTGATGG AAATGTCTGG ATCATTCCGG
  251 TTGTGCGTAC TTTGAGATTT GNGTTTGGGG ATGTNCATTG TGTTTGACAG
  301 CACTTTTTTN ATCCCTAATG TNAAATGCNT NATTTGATTG TGANTTGGGG
  351 GTNACATTG GTNAAGGNTN CCCNTNTGAC ACAGTAGNTG GTNCCCGACT
  401 TANAATNGNN GAANANGATG NATNANGAAC CTTTTTTTGG GTGGGGGGGT
  451 NNCGGGGCAG TNNAANGNNG NCTCCCCAGG TTTGGNGTNG CAATNGNGGA
  501 ANNNTGG

HSBBU76R
    1 TTTTTTTTGT AGATGGATCT TACAATGTAG CCCAAATAAA TAAATAAAGC
   51 ATTTACATTA GGATAAAAAA GTGCTGTGAA AACAATGACA TCCCAAACCA
  101 AATCTCAAAG TACGCACAAA CGGAATGATC CAGACATTTC CATAGNGTCC
  151 TTATTATCAC ATTCAGCTTA TAAAANTAAT GCCAAGTGCA GTGAAAAGTT
  201 ACAGGATGTT CCATCCACTG GGTGGATT

FIG.4

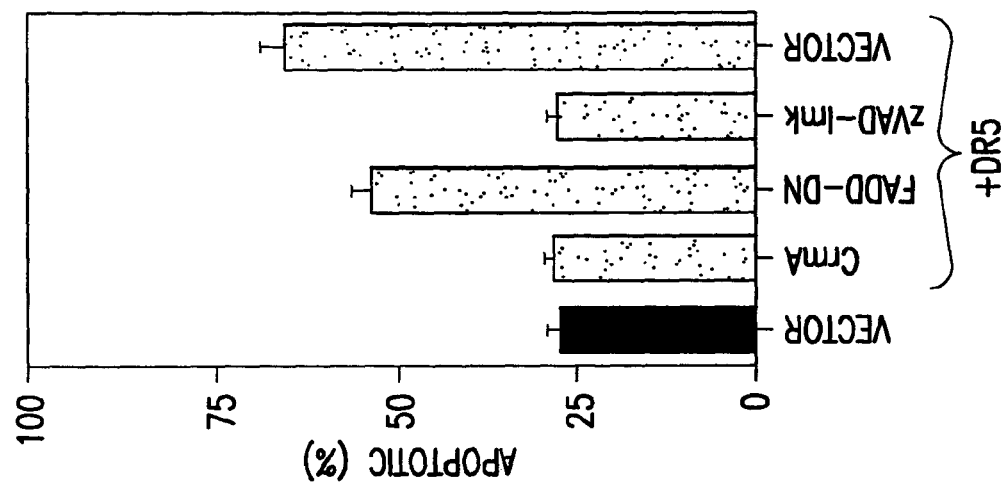
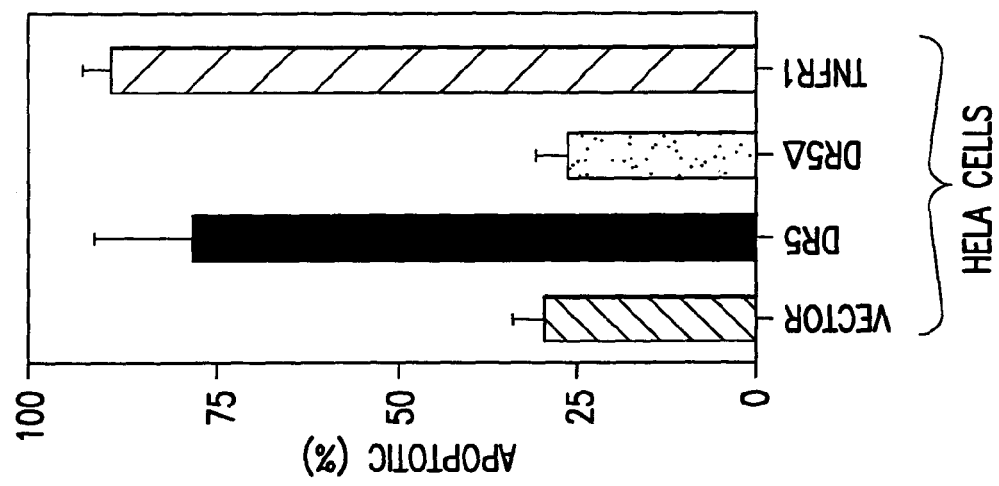
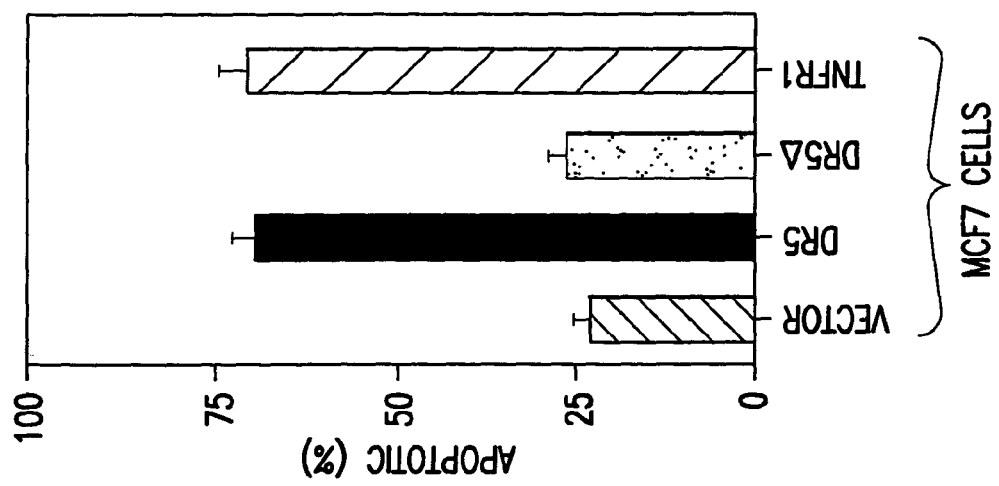

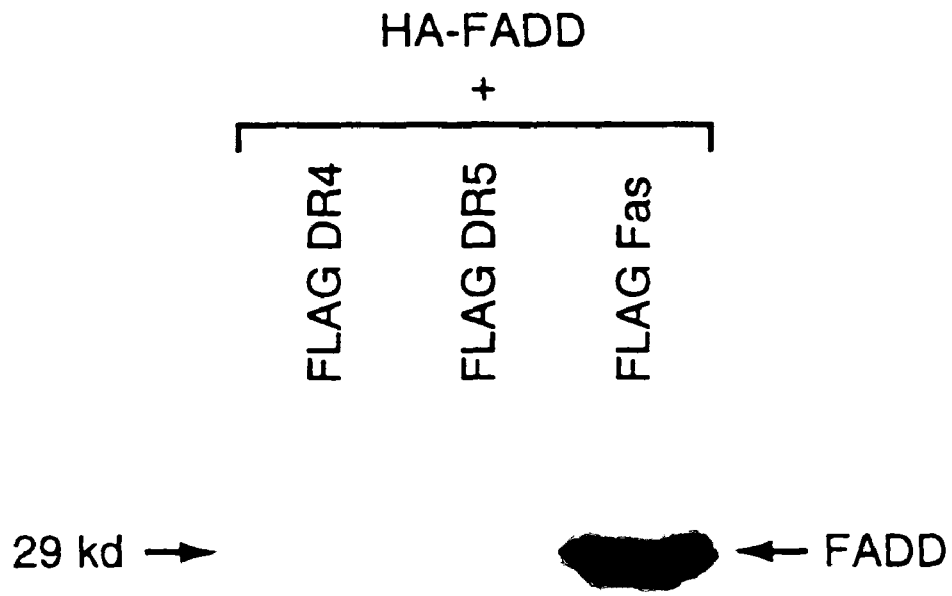
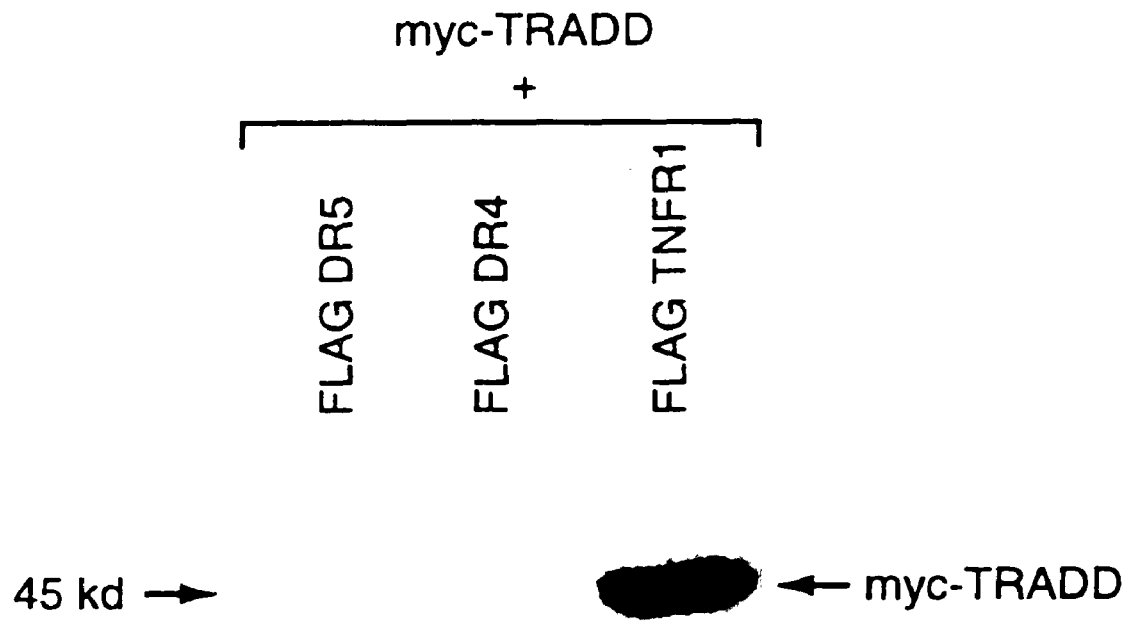
FIG.5D

DEATH DOMAIN CONTAINING RECEPTOR 5

This application claims benefit of 35 U.S.C. Section 119(e) based on U.S. Provisional Application Ser. Nos. 60/040,846, filed Mar. 17, 1997 and 60/054,021, filed Jul. 29, 1997, both of which are incorporated herein by reference.

BACKGROUND OF THE INVENTION

1. Field of the Invention

The present invention relates to a novel member of the tumor necrosis factor family of receptors. More specifically, isolated nucleic acid molecules are provided encoding human Death Domain Containing Receptor 5, or simply "DR5." DR5 polypeptides are also provided, as are vectors, host cells, and recombinant methods for producing the same. The invention further relates to screening methods for identifying agonists and antagonists of DR5 activity.

2. Related Art

Numerous biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands, there are included TNF-α, lymphotoxin-α (LT-α, also known as TNF-β, LT-β (found in complex heterotrimer LT-α2-β, FasL, CD40L, CD27L, CD30L, 4-IBBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-IBB, OX40, low affinity p75 and NGF-receptor (Meager, A., *Biologicals,* 22:291-295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., *Science* 259:990 (1993)). Targeted mutations of the low affinity nerve growth factor receptor cause a disorder characterized by faulty sensory innovation of peripheral structures (Lee, K. F. et al., *Cell* 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., *Science* 264:667-668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential for the normal development and homeostasis of multicellular organisms (H. Steller, *Science* 267:1445-1449 (1995)). Derangements of apoptosis contribute to the pathogenesis of several human diseases including cancer, neurodegenerative disorders, and acquired immune deficiency syndrome (C. B. Thompson, *Science* 267:1456-1462 (1995)). Recently, much attention has focused on the signal transduction and biological function of two cell surface death receptors, Fas/APO-1 and TNFR-1 (J. L. Cleveland et al., *Cell* 81:479-482 (1995); A. Fraser, et al., *Cell* 85:781-784 (1996); S. Nagata et al., *Science* 267:1449-56 (1995)). Both are members of the TNF receptor family which also include TNFR-2, low affinity NGFR, CD40, and CD30, among others (C. A. Smith et al., *Science* 248:1019-23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the *Drosophila* suicide gene, reaper (P. Golstein, et al., *Cell* 81:185-186 (1995); K. White et al., *Science* 264:677-83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., *Cell* 81: 505-12 (1995); M. P. Boldin et al., *J. Biol Chem* 270:7795-8 (1995); F. C. Kischkel et al., *EMBO* 14:5579-5588 (1995)), which in turn binds and presumably activates FLICE/MACH1, a member of the ICE/CED-3 family of pro-apoptotic proteases (M. Muzio et al., *Cell* 85:817-827 (1996); M. P. Boldin et al., *Cell* 85:803-815 (1996)). While the central role of Fas/APO-1 is to trigger cell death, TNFR-1 can signal an array of diverse biological activities-many of which stem from its ability to activate NF-kB (L. A. Tartaglia et al., *Immunol Today* 13:151-3 (1992)). Accordingly, TNFR-1 recruits the multivalent adapter molecule TRADD, which like FADD, also contains a death domain (H. Hsu et al., *Cell* 81:495-504 (1995); H. Hsu, et al., *Cell* 84:299-308 (1996)). Through its associations with a number of signaling molecules including FADD, TRAF2, and RIP, TRADD can signal both apoptosis and NF-kB activation (H. Hsu et al., *Cell* 84:299-308 (1996); H. Hsu, et al., *Immunity* 4:387-396 (1996)).

Recently, a new apoptosis-inducing TNF ligand has been discovered. S. R. Wiley et al. (*Immunity* 3:673-682 (1995)) named the molecule—"TNF-related apoptosis-inducing ligand" or simply "TRAIL." The molecule was also called "Apo-2 ligand" or "Apo-2L." R. M. Pitt et al., *J. Biol. Chem.* 271:12687-12690 (1996).

This molecule was also disclosed in U.S. provisional application No. 60/013,405. For convenience, the molecule will be referred to herein as TRAIL.

Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and is constitutively transcribed by some cell lines. It has been shown that TRAIL acts independently from the Fas ligand (Wiley et al., supra). It has also been shown that TRAIL activates apoptosis rapidly, within a time frame that is similar to death signaling by Fas/Apo-1L, but much faster than TNF-induced apoptosis. S. A. Marsters et al., *Current Biology* 6:750-752 (1996). The inability of TRAIL to bind TNFR-1, Fas, or the recently identified DR3, suggests that TRAIL may interact with a unique receptor(s).

Several unique receptors for TRAIL have already been identified. In U.S. Provisional Patent application No. 60/035,722, DR4, a novel death domain containing receptor for TRAIL, was disclosed. See, Pan et al., *Science* 276:111-113 (April, 1997). The TR5 receptor, the subject of U.S. provisional patent application 60/035,496, has now been shown to bind TRAIL. In U.S. provisional patent application No. 60/050,936, it was predicted that the TR10 receptor would also bind TRAIL, owing to sequence homology with DR4.

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize additional novel receptors that bind TRAIL.

SUMMARY OF THE INVENTION

The present invention provides for isolated nucleic acid molecules comprising nucleic acid sequences encoding the amino acid sequence shown in FIGS. 1A and 1B (SEQ ID NO:2) or the amino acid sequence encoded by the cDNA clone deposited as ATCC Deposit No. 97920 on Mar. 7, 1997.

The present invention also provides recombinant vectors, which include the isolated nucleic acid molecules of the invention, and to host cells containing the recombinant vectors, as well as to methods of making such vectors and host cells and for using them for production of DR5 polypeptides or peptides by recombinant techniques.

The invention further provides an isolated DR5 polypeptide having an amino acid sequence encoded by a polynucleotide described herein.

The present invention also provides diagnostic assays such as quantitative and diagnostic assays for detecting levels of DR5 protein. Thus, for instance, a diagnostic assay in accordance with the invention for detecting over-expression of DR5, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis—programmed cell death—is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft versus host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, which involves administering to a cell which expresses the DR5 polypeptide an effective amount of an agonist capable of increasing DR5 mediated signaling. Preferably, DR5 mediated signaling is increased to treat a disease wherein decreased apoptosis is exhibited.

In a further aspect, the present invention is directed to a method for inhibiting apoptosis induced by a TNF-family ligand, which involves administering to a cell which expresses the DR5 polypeptide an effective amount of an antagonist capable of decreasing DR5 mediated signaling. Preferably, DR5 mediated signaling is decreased to treat a disease wherein increased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the DR5 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the DR5 polypeptide can be contacted with either an endogenous or exogenously administered TNF-family ligand.

BRIEF DESCRIPTION OF THE FIGURES

FIGS. 1A and 1B show the nucleotide (SEQ ID NO:1) and deduced amino acid sequence (SEQ ID NO:2) of DR5. It is predicted that amino acids 1-51 (underlined) constitute the signal peptide (amino acid residues from about −51 to about −1 in SEQ ID NO:2); amino acids 52-184 constitute the extracellular domain (amino acid residues from about 1 to about 133 in SEQ ID NO:2); amino acids 185-208 (underlined) constitute the transmembrane domain (amino acid residues from about 134 to about 157 in SEQ ID NO:2); and amino acids 209-411 constitute the intracellular domain (amino acid residues from about 158 to about 360 in SEQ ID NO:2), of which amino acids 324-391 (italicized) constitute the death domain (amino acid residues from about 273 to about 340 in SEQ ID NO:2).

FIGS. 2A, 2B, and 2C show the regions of similarity between the amino acid sequences of DR5 (HLYBX88), human tumor necrosis factor receptor 1 (h TNFR1) (SEQ ID NO:3), human Fas protein (SEQ ID NO:4), and the death domain containing receptor 3 (SEQ ID NO:5). The comparison was created with the Megalign program which is contained in the DNA Star suite of programs, using the Clustal method.

FIG. 4 shows the nucleotide sequences (HAPBU13R (SEQ ID NO:6) and HSBBU76R (SEQ ID NO:7)) of two cDNA molecules which are related to the nucleotide sequence shown in FIGS. 1A and 1B (SEQ ID NO:1).

FIG. 5A is a bar graph showing that overexpression of DR5 induced apoptosis in MCF7 human breast carcinoma cells. FIG. 5B is a bar graph showing that overexpression of DR5 induced apoptosis in human epitheloid carcinoma (Hela) cells. FIG. 5C is a bar graph showing that DR5-induced apoptosis was blocked by caspase inhibitors, CrmA and z-VAD-fmk, but dominant negative FADD was without effect. FIG. 5D is an immunoblot showing that, like DR4, DR5 did not interact with FADD and TRADD in vivo.

DETAILED DESCRIPTION OF THE PREFERRED EMBODIMENTS

Figure 2A:
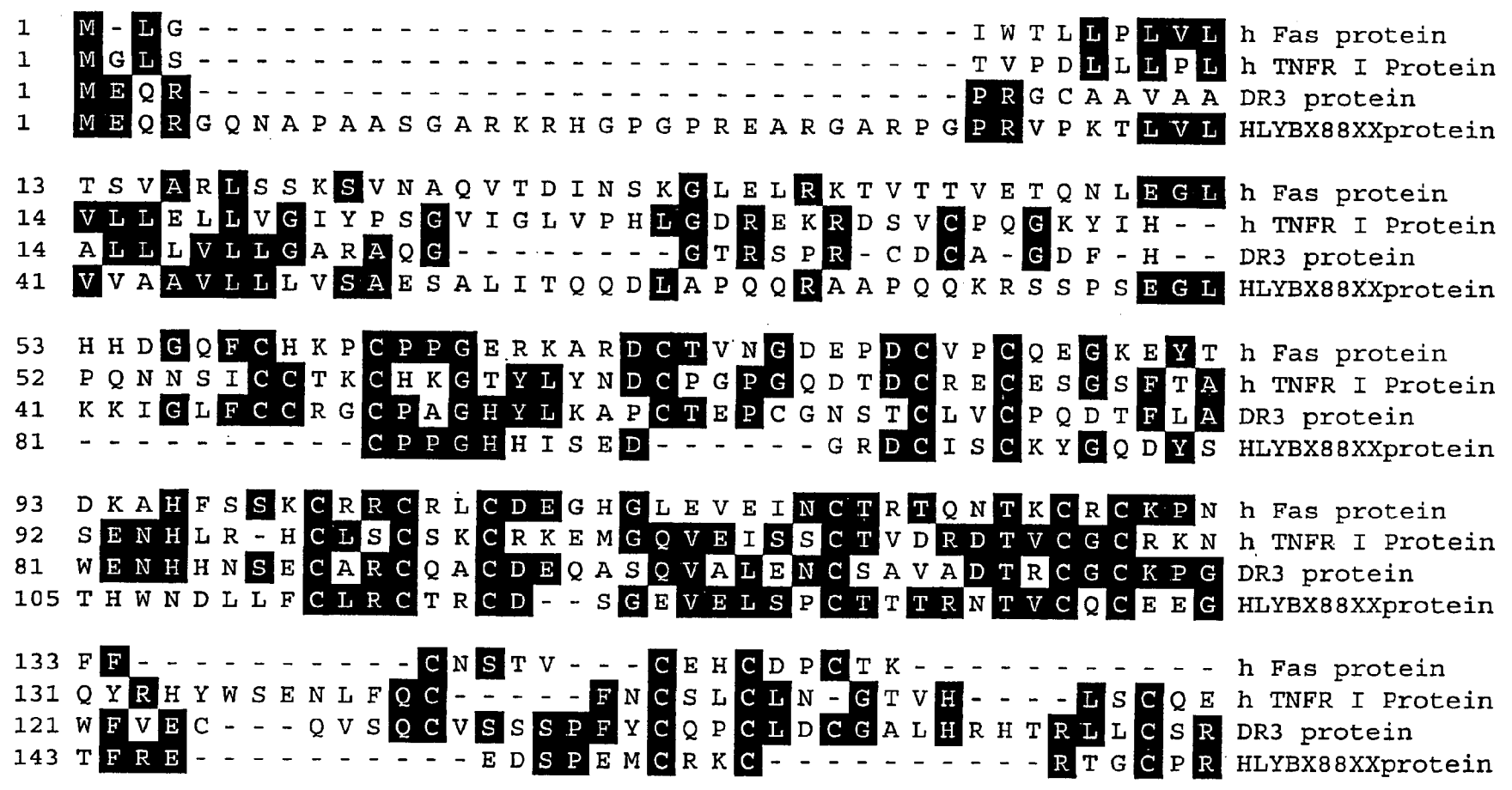
Figure 2B:
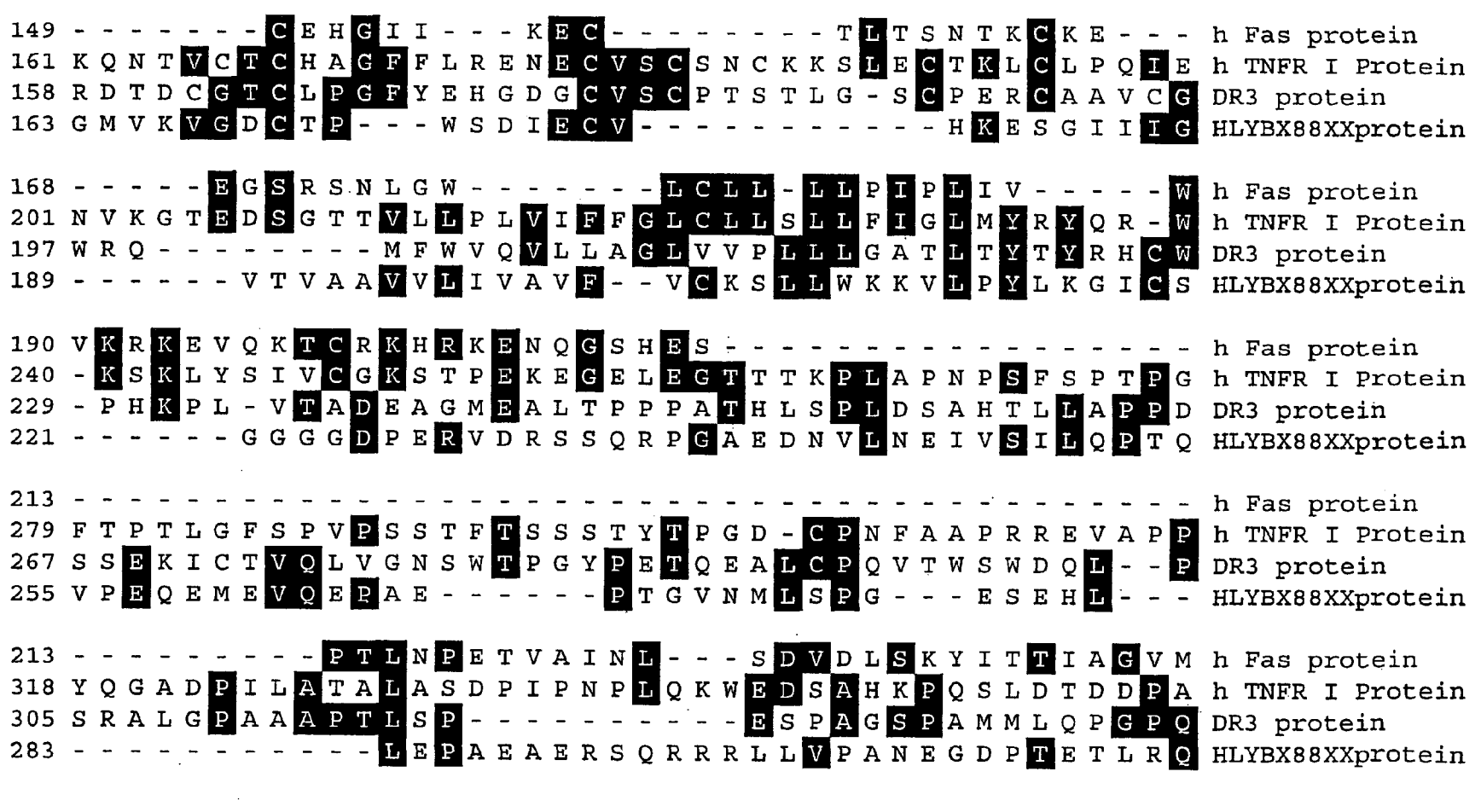
Figure 3:
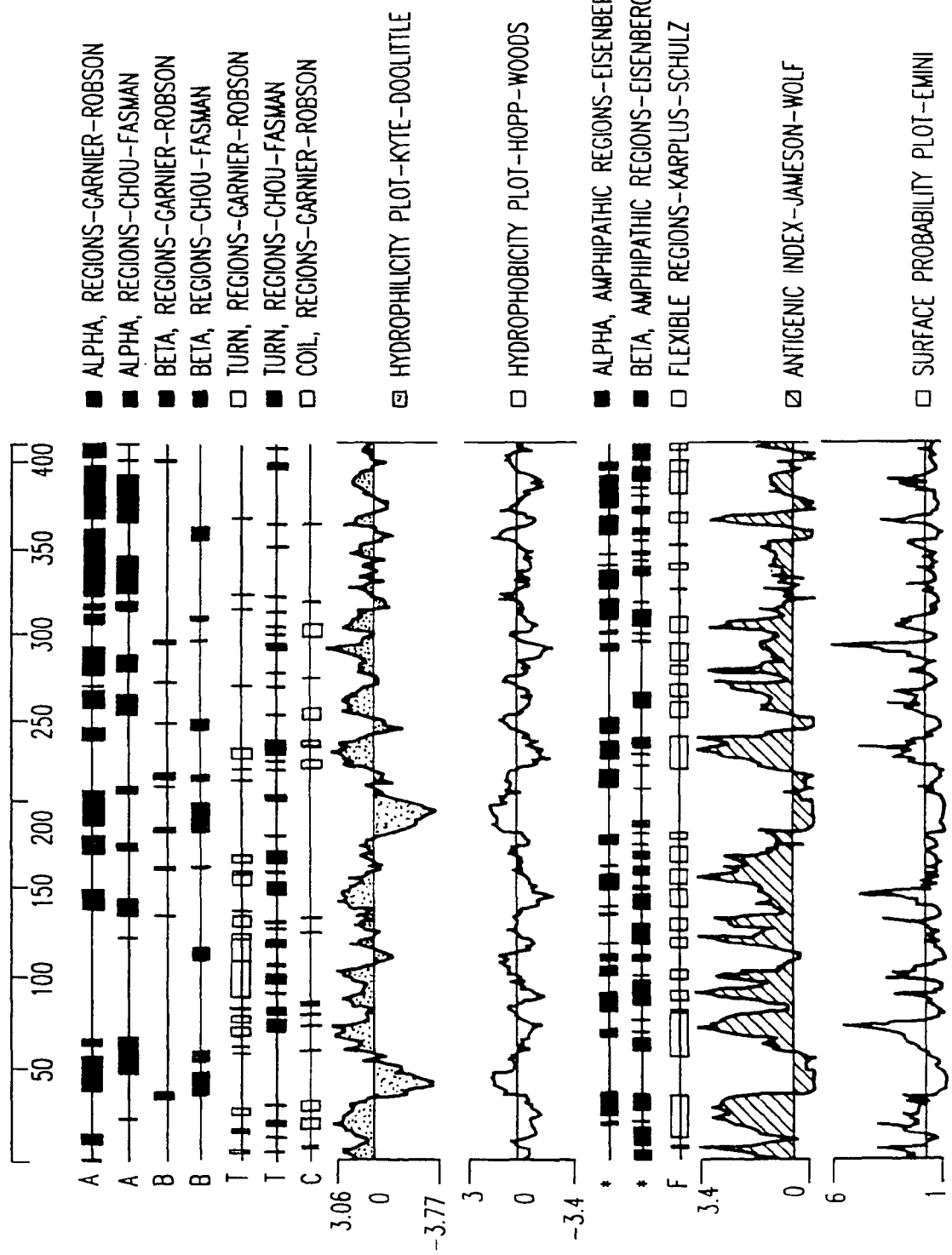
FIG. 3 shows an analysis of the DR5 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 62 to about 110, about 119 to about 164, about 224 to about 271, and about 275 to about 370 as depicted in FIGS. 1A and 1B (SEQ ID NO:2) correspond to the shown highly antigenic regions of the DR5 protein. These highly antigenic fragments in FIGS. 1A and 1B (SEQ ID NO:2) correspond to the following fragments, respectively, in SEQ ID NO:2: amino acid residues from about 11 to about 59, from about 68 to about 113, from about 173 to about 220, and from about 224 to about 319.

The present invention provides isolated nucleic acid molecules comprising a polynucleotide encoding a DR5 polypeptide having the amino acid sequence shown in FIGS. 1A and 1B (SEQ ID NO:2), or a fragment of the polypeptide. The DR5 polypeptide of the present invention shares sequence homology with other known death domain containing receptors of the TNFR family including human TNFR-I, DR3 and Fas (FIGS. 2A, 2B, and 2C). The nucleotide sequence shown in FIGS. 1A and 1B (SEQ ID NO:1) was obtained by sequencing cDNA clones such as HLYBX88, which was deposited on Mar. 7, 1997 at the American Type Culture Collection, 10801 University Boulevard, Manassas, Va. 20110-2209, and given Accession Number 97920. The deposited clone is contained in the pSport 1 plasmid (Life Technologies, Gaithersburg, Md.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleic acid sequence set out in SEQ ID NO:1, a nucleic acid molecule of the present invention encoding a DR5 polypeptide may be obtained using standard cloning and screening procedures, such as those for cloning cDNAs using mRNA as starting material. Illustrative of the invention, the nucleic acid molecule of the invention has been identified in cDNA libraries of the following tissues: primary dendritic cells, endothelial tissue, spleen, chronic lymphocytic leukemia, and human thymus stromal cells.

The determined nucleotide sequence of the DR5 cDNA of SEQ ID NO:1 contains an open reading frame encoding a protein of about 411 amino acid residues whose initiation codon is at position 130-132 of the nucleotide sequence shown in FIGS. 1A and 1B (SEQ ID NO.1), with a leader sequence of about 51 amino acid residues. Of known members of the TNF receptor family, the DR5 polypeptide of the invention shares the greatest degree of homology with human TNFR1, FAS and DR3 polypeptides shown in FIGS. 2A, 2B, and 2C, including significant sequence homology over multiple cysteine-rich domains. The homology DR5 shows to other death domain containing receptors strongly indicates that DR5 is also a death domain containing receptor with the ability to induce apoptosis. DR5 has also now been shown to bind TRAIL.

As indicated, the present invention also provides the mature form(s) of the DR5 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature DR5 polypeptide having the amino acid sequence encoded by the cDNA clone contained in the host identified as ATCC Deposit No. 97920, and as shown in FIGS. 1A and 1B (SEQ ID NO:2). By the mature DR5 protein having the amino acid sequence encoded by the cDNA clones contained in the host identified as ATCC Deposit No 97920, is meant the mature form(s) of the DR5 protein produced by expression in a mammalian cell (e.g., COS cells, as described below) of the complete open reading frame encoded by the human DNA sequence of the clone contained in the vector in the deposited host. As indicated below, the mature DR5 having the amino acid sequence encoded by the cDNA clone contained in ATCC Deposit No. 97920, may or may not differ from the predicted "mature" DR5 protein shown in SEQ ID NO:2 (amino acids from about 1 to about 360) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271-286 (1985)) and von Heinje (*Nucleic Acids Res.* 14: 4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete DR5 polypeptide of the present invention was analyzed by a computer program ("PSORT"). See, K. Nakai and M. Kanehisa, *Genomics* 14:897-911 (1992). PSORT is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 51 and 52 in FIGS. 1A and 1B (−1 and 1 in SEQ ID NO:2). Thereafter, the complete amino acid sequences were further analyzed by visual inspection, applying a simple form of the (−1,−3) rule of von Heinje. von Heinje, supra. Thus, the leader sequence for the DR5 protein is predicted to consist of amino acid residues from about 1 to about 51, underlined in FIGS. 1A and 1B (corresponding to about −51 to about −1 in SEQ ID NO:2), while the predicted mature DR5 protein consists of residues from about 52 to about 411 in FIGS. 1A and 1B (corresponding to about 1 to about 360 in SEQ ID NO:2).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DR5DNA molecules comprising an open reading frame (ORF) shown in SEQ ID NO:1; DNA molecules comprising the coding sequence for the mature DR5 protein; and DNA molecules which comprise a sequence substantially different from those described above, but which, due to the degeneracy of the genetic code, still encode the DR5 protein. Of course, the genetic code is well known in the art. Thus, it would be routine for one skilled in the art to generate such degenerate variants.

In another aspect, the invention provides isolated nucleic acid molecules encoding the DR5 polypeptide having an amino acid sequence encoded by the cDNA clone contained in the plasmid deposited as ATCC Deposit No. 97920 on Mar. 7, 1997. In a further embodiment, nucleic acid molecules are provided that encode the mature DR5 polypeptide or the full length DR5 polypeptide lacking the N-terminal methionine. The invention further provides an isolated nucleic acid molecule having the nucleotide sequence shown in SEQ ID NO:1 or the nucleotide sequence of the DR5 cDNA contained in the above-described deposited clone, or a nucleic acid molecule having a sequence complementary to one of the above sequences. Such isolated molecules, particularly DNA molecules, are useful as probes for gene mapping by in situ hybridization with chromosomes, and for detecting expression of the DR5 gene in human tissue, for instance, by Northern blot analysis The present invention is further directed to fragments of the isolated nucleic acid molecules described herein. By a fragment of an isolated DNA molecule having the nucleotide sequence of the deposited cDNA, the nucleotide sequence shown in SEQ ID NO:1, or the complementary strand thereto, is intended DNA fragments at least about 15 nt, and more preferably at least 20 nt, still more preferably at least about 30 nt, and even more preferably, at least about 40, 50, 100, 150, 200, 250, 300, 400, or 500 nt in length. These fragments have numerous uses which include, but are not limited to, diagnostic probes and primers as discussed herein. Of course larger DNA fragments 500-1500 nt in length are also useful according to the present invention, as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited DNA or the nucleotide sequence as shown in SEQ ID NO:1.

Preferred nucleic acid fragments of the present invention include, but are not limited to nucleic acid molecules encoding: a polypeptide comprising the DR5 extracellular domain (amino acid residues from about 52 to about 184 in FIGS. 1A and 1B (from about 1 to about 133 in SEQ ID NO:2)); a polypeptide comprising the DR5 transmembrane domain (amino acid residues from about 185 to about 208 in FIGS. 1A and 1B (from about 134 to about 157 in SEQ ID NO:2)); a polypeptide comprising the DR5 intracellular domain (amino acid residues from about 209 to about 411 in FIGS. 1A and 1B (from about 158 to about 360 in SEQ ID NO:2)); and a polypeptide comprising the DR5 death domain (amino acid residues from about 324 to about 391 in FIGS. 1A and 1B (from about 273 to about 340 in SEQ ID NO:2)). Since the location of these domains have been predicted by computer graphics, one of ordinary skill would appreciate that the amino acid residues constituting these domains may vary slightly (e.g., by about 1 to 15 residues) depending on the criteria used to define each domain.

Preferred nucleic acid fragments of the invention encode a full-length DR5 polypeptide lacking the nucleotides encoding the amino-terminal methionine (nucleotides 130-132 in SEQ ID NO:1) as it is known that the methionine is cleaved naturally and such sequences maybe useful in genetically engineering DR5 expression vectors. Polypeptides encoded by such polynucleotides are also contemplated by the invention.

Preferred nucleic acid fragments of the present invention further include nucleic acid molecules encoding epitope-bearing portions of the DR5 protein. In particular, such nucleic acid fragments of the present invention include, but are not limited to, nucleic acid molecules encoding: a polypeptide comprising amino acid residues from about 62 to about 110 in FIGS. 1A and 1B (about 11 to about 59 in SEQ ID NO:2); a polypeptide comprising amino acid residues from about 119 to about 164 in FIGS. 1A and 1B (about 68 to about 113 in SEQ ID NO:2); a polypeptide comprising amino acid residues from about 224 to about 271 in FIGS. 1A and 1B (about 173 to about 220 in SEQ ID NO:2); and a polypeptide comprising amino acid residues from about 275 to about 370 in FIGS. 1A and 1B (about 224 to about 319 in SEQ ID NO:2). The inventors have determined that the above polypeptide fragments are antigenic regions of the DR5 protein. Methods for determining other such epitope-bearing portions of the DR5 protein are described in detail below.

In addition, the invention provides nucleic acid molecules having nucleotide sequences related to extensive portions of SEQ ID NO:1 which have been determined from the following related cDNA clones: HAPBU13R (SEQ ID NO:6) and HSBBU76R (SEQ ID NO:7). The nucleotide sequences of HAPBU13R and HSBBU76R are shown in FIG. 4.

Further, the invention includes a polynucleotide comprising any portion of at least about 30 nucleotides, preferably at least about 50 nucleotides, of SEQ ID NO:1 from residue 284 to 1,362, preferably from 284 to 681.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposit No. 97920. By "stringent hybridization conditions" is intended overnight incubation at 42° C. in a solution comprising: 50% formamide, 5×SSC (750 mM NaCl, 75 mM trisodium citrate 10801 University Boulevard, Manassas, Va. 20110-2209), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 or 80-150 nt, or the entire length of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1).

Of course, a polynucleotide which hybridizes only to a poly A sequence (such as the 3' terminal poly(A) tract of the DR5 cDNA shown in FIGS. 1A and 1B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a DR5 polypeptide may include, but are not limited to, the coding sequence for the mature polypeptide, by itself; the coding sequence for the mature polypeptide and additional sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767-778(1984). As discussed below, other such fusion proteins include the DR5 receptor fused to Fc at the N- or C-terminus.

The present invention further relates to variants of the nucleic acid molecules of the present invention, which encode portions, analogs, or derivatives of the DR5 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions or additions. Especially preferred among these are silent substitutions, additions, and deletions, which do not alter the properties and activities of the DR5 receptor or portions thereof. Also especially preferred in this regard are conservative substitutions.

Further embodiments of the invention include isolated nucleic acid molecules that are at least 90% identical, and more preferably at least 95%, 96%, 97%, 98% or 99% identical, to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the amino terminal methionine; (c) a nucleotide sequence encoding the polypeptide having the amino acid sequence at positions about 1 to about 360 in SEQ ID NO:2; (d) a nucleotide sequence encoding the polypeptide having the amino acid sequence encoded by the cDNA clone contained in ATCC Deposit No. 97920; (e) a nucleotide sequence encoding the mature DR5 polypeptide having the amino acid sequence encoded by the cDNA clone contained in ATCC Deposit No. 97920; (1) a nucleotide sequence that encodes the DR5 extracellular domain having the amino acid sequence at positions about 1 to about 133 in SEQ ID NO:2, or the DR5 extracellular domain encoded by the cDNA contained in ATCC Deposit No. 97920; (g) a nucleotide sequence that encodes the DR5 transmembrane domain having the amino acid sequence at positions about 134 to about 157 of SEQ ID NO:2, or the DR5 transmembrane domain encoded by the cDNA contained in ATCC Deposit No. 97920; (h) a nucleotide sequence that encodes the DR5 intracellular domain having the amino acid sequence at positions about 158 to about 360 of SEQ ID NO:2, or the DR5 intracellular domain encoded by the cDNA contained in ATCC Deposit No. 97920; (i) a nucleotide sequence that encodes the DR5 death domain having the amino acid sequence at positions about 273 to about 340 of SEQ ID NO:2, or the DR5 death domain encoded by the cDNA contained in ATCC Deposit No. 97920; and (j) a nucleotide sequence complementary to any of the nucleotide sequences in (a), (b), (c), (d), (e), (f), (g), (h), or (i) above.

By a polynucleotide having a nucleotide sequence at least, for example, 95% "identical" to a reference nucleotide sequence encoding a DR5 polypeptide is intended that the nucleotide sequence of the polynucleotide is identical to the reference sequence except that the polynucleotide sequence may include up to five point mutations per each 100 nucleotides of the reference nucleotide sequence encoding the DR5 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be the entire DR5 nucleotide sequence shown in FIGS. 1A and 1B (SEQ ID NO:1) or any polynucleotide fragment as described herein.

As a practical matter, whether any particular nucleic acid molecule is at least 90%, 95%, 96%, 97%, 98% or 99% identical to, for instance, the nucleotide sequence shown in SEQ ID NO:1 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to the nucleic acid sequence shown in SEQ ID NO:1, the nucleic acid sequence of the deposited cDNAs, or fragments thereof, irrespective of whether they encode a polypeptide having DR5 activity. This is because even where a particular nucleic acid molecule does not encode a polypeptide having DR5 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DR5 activity include, inter alia: (1) isolating the DR5 gene or allelic variants thereof in a cDNA library; (2) in situ hybridization (e.g., "FISH") to metaphase chromosomal spreads to provide precise chromosomal location of the DR5 gene, as described in Verma et al., Human Chromosomes: *A Manual of Basic Techniques*, Pergamon Press, New York (1988); and (3) Northern Blot analysis for detecting DR5 mRNA expression in specific tissues.

Preferred, however, are nucleic acid molecules having sequences at least 90%, 95%, 96%, 97%, 98% or 99% identical to the nucleic acid sequence shown in SEQ ID NO:1, the nucleic acid sequence of the deposited cDNAs, or fragments thereof, which do, in fact, encode a polypeptide having DR5 protein activity. By "a polypeptide having DR5 activity" is intended polypeptides exhibiting activity similar, but not necessarily identical, to an activity of the DR5 protein of the invention (either the full-length protein or, preferably, the mature protein), as measured in a particular biological assay. For example, DR5 protein activity can be measured using the cell death assays performed essentially as previously described (A. M. Chinnaiyan, et al., *Cell* 81:505-12 (1995); M. P. Boldin, et al., *J Biol Chem* 270:7795-8 (1995); F. C. Kischkel, et al., *EMBO* 14:5579-5588 (1995); A. M. Chinnaiyan, et al., *J Biol Chem* 271:4961-4965 (1996)) and as set forth in Example 5, below. In MCF7 cells, plasmids encoding full-length DR5 or a candidate death domain containing receptor are co-transfected with the pLantern reporter construct encoding green fluorescent protein. Nuclei of cells transfected with DR5 will exhibit apoptotic morphology as assessed by DAPI staining. Similar to TNFR-1 and Fas/APO-1 (M. Muzio, et al., *Cell* 85:817-827 (1996); M. P. Boldin, et al., *Cell* 85:803-815 (1996); M. Tewari, et al., *J Biol Chem* 270:3255-60 (1995)), DR5-induced apoptosis is preferably blocked by the inhibitors of ICE-like proteases, CrmA and z-VAD-fmk.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in SEQ ID NO:1, or fragments thereof, will encode a polypeptide "having DR5 protein activity." In fact, since degenerate variants of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having DR5 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences Tolerance to Amino Acid Substitutions," *Science* 247:1306-1310 (1990), wherein the authors indicate that proteins are surprisingly tolerant of amino acid substitutions.

Polynucleotide Assays

This invention is also related to the use of the DR5 polynucleotides to detect complementary polynucleotides such as, for example, as a diagnostic reagent. Detection of a mutated form of DR5 associated with a dysfunction will provide a diagnostic tool that can add or define a diagnosis of a disease or susceptibility to a disease which results from under-expression over-expression or altered expression of DR5 or a soluble form thereof, such as, for example, tumors or autoimmune disease.

Individuals carrying mutations in the DR5 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163-166 (1986)). RNA or cDNA may also be used in the same ways. As an example, PCR primers complementary to the nucleic acid encoding DR5 can be used to identify and analyze DR5 expression and mutations. For example, deletions and insertions can be detected by a change in size of the amplified product in comparison to the normal genotype. Point mutations can be identified by hybridizing amplified DNA to radiolabeled DR5 RNA or alternatively, radiolabeled DR5 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and Sl protection or the chemical cleavage method (e.g., Cotton et al., *Proc. Natl. Acad. Sci. USA* 85: 4397-4401 (1985)).

Thus, the detection of a specific DNA sequence may be achieved by methods which include, but are not limited to, hybridization, RNase protection, chemical cleavage, direct DNA sequencing or the use of restriction enzymes, (e.g., restriction fragment length polymorphisms ("RFLP") and Southern blotting of genomic DNA).

In addition to more conventional gel-electrophoresis and DNA sequencing, mutations also can be detected by in situ analysis.

Vectors and Host Cells

The present invention also relates to vectors which include DNA molecules of the present invention, host cells which are genetically engineered with vectors of the invention and the production of polypeptides of the invention by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The DNA sequence in the expression vector is operatively linked to appropriate expression control sequence(s)), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. In general, expression constructs will contain sites for transcription, initiation and termination, and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Such markers include, but are not limited to, dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors available to those of skill in the art.

Selection of appropriate vectors and promoters for expression in a host cell is a well known procedure and the requisite techniques for expression vector construction, introduction of the vector into the hosts and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

The polypeptide may be expressed in a modified form, such as a fusion protein (comprising the polypeptide joined via a peptide bond to a heterologous protein sequence (of a different protein)), and may include not only secretion signals but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification or during subsequent handling and storage. Additionally, a region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition,* 8:52-58 (1995) and K. Johanson et al., *The Journal of Biological Chemistry,* 270: 9459-9471 (1995).

The DR5 polypeptides can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

DR5 polynucleotides and polypeptides may be used in accordance with the present invention for a variety of applications, particularly those that make use of the chemical and biological properties of DR5. Among these are applications in treatment of tumors, resistance to parasites, bacteria and viruses, to induce proliferation of T-cells, endothelial cells and certain hematopoietic cells, to treat restenosis, graft vs. host disease, to regulate anti-viral responses and to prevent certain autoimmune diseases after stimulation of DR5 by an agonist. Additional applications relate to diagnosis and to treatment of disorders of cells, tissues and organisms. These aspects of the invention are discussed further below.

DR5Polypeptides and Fragments

The invention further provides an isolated DR5 polypeptide having the amino acid sequence encoded by the deposited cDNA, or the amino acid sequence in SEQ ID NO:2, or a polypeptide or peptide comprising a portion of the above polypeptides.

It will be recognized in the art that some amino acid sequence of DR5 can be varied without significant effect on the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes variations of the DR5 protein which show substantial DR5 protein activity or which include regions of DR5, such as the protein portions discussed below. Such mutants include deletions, insertions, inversions, repeats, and type substitutions. As indicated above, guidance concerning which amino acid changes are likely to be phenotypically silent can be found in Bowie, J. U. et al., *Science* 247:1306-1310 (1990).

Thus, the fragment, derivative, or analog of the polypeptide of SEQ ID NO:2, or that encoded by the deposited cDNA, may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acids and with neutral or negatively charged amino acids. The latter results in proteins with reduced positive charge to improve the characteristics of the DR5 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the DR5 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions | |
| --- | --- |
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

Amino acids in the DR5 protein of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the DR5 polypeptide can be substantially purified by the one-step method described in Smith and Johnson, *Gene* 67:31-40 (1988).

The polypeptides of the present invention also include the polypeptide encoded by the deposited cDNA including the leader; the mature polypeptide encoded by the deposited the cDNA minus the leader (i.e., the mature protein); a polypeptide comprising amino acids about −51 to about 360 in SEQ ID NO:2; a polypeptide comprising amino acids about −50 to about 360 in SEQ ID NO:2; a polypeptide comprising amino acids about 1 to about 360 in SEQ ID NO:2; a polypeptide comprising the extracellular domain; a polypeptide comprising the transmembrane domain; a polypeptide comprising the intracellular domain; a polypeptide comprising the extracellular and intracellular domains with all or part of the transmembrane domain deleted; and a polypeptide comprising the death domain; as well as polypeptides which are at least 80% identical, more preferably at least 90% or 95% identical, still more preferably at least 96%, 97%, 98%, or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a DR5 polypeptide is intended that the amino acid sequence of the polypeptide is identical to the reference sequence except that the polypeptide sequence may include up to five amino acid alterations per each 100 amino acids of the reference amino acid of the DR5 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and 1B (SEQ ID NO:2), the amino acid sequence encoded by deposited cDNA clones, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptide of the present invention could be used as a molecular weight marker on SDS-PAGE gels or on molecular sieve gel filtration columns using methods well known to those of skill in the art.

The present inventors have discovered that the DR5 polypeptide is a 411 residue protein exhibiting three main structural domains. First, the ligand binding domain was identified within residues from about 52 to about 184 in FIGS. 1A and 1B (amino acid residues from about 1 to about 133 in SEQ ID NO:2). Second, the transmembrane domain was identified within residues from about 185 to about 208 in FIGS. 1A and 1B (amino acid residues from about 134 to about 157 in SEQ ID NO:2). Third, the intracellular domain was identified within residues from about 209 to about 411 in FIGS. 1A and 1B (amino acid residues from about 158 to about 360 in SEQ ID NO:2). Importantly, the intracellular domain includes a death domain at residues from about 324 to about 391 (amino acid residues from about 273 to about 340 in SEQ ID NO:2). Further preferred fragments of the polypeptide shown in FIGS. 1A and 113 include the mature protein from residues about 52 to about 411 (amino acid residues from about 1 to about 360 in SEQ ID NO:2), and soluble polypeptides comprising all or part of the extracellular and intracellular domains but lacking the transmembrane domain.

The invention further provides DR5 polypeptides encoded by the deposited cDNA clone including the leader and DR5 polypeptide fragments selected from the mature protein, the extracellular domain, the transmembrane domain, the intracellular domain, the death domain, and all combinations thereof.

In another aspect, the invention provides a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A., "Antibodies That React With Predetermined Sites on Proteins," *Science* 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777. Antigenic epitope-bearing peptides and polypeptides of the invention preferably contain a sequence of at least seven, more preferably at least nine, and most preferably between at least about 15 to about 30 amino acids contained within the amino acid sequence of a polypeptide of the invention.

Non-limiting examples of antigenic polypeptides or peptides that can be used to generate DR5-specific antibodies include: a polypeptide comprising amino acid residues from about 62 to about 110 in FIGS. 1A and 1B (about 11 to about 59 in SEQ ID NO:2); a polypeptide comprising amino acid residues from about 119 to about 164 in FIGS. 1A and 1B (about 68 to about 113 in SEQ ID NO:2); a polypeptide comprising amino acid residues from about 224 to about 271 in FIGS. 1A and 1B (about 173 to about 220 in SEQ ID NO:2); and a polypeptide comprising amino acid residues from about 275 to about 370 in FIGS. 1A and 1B (about 224 to about 319 in SEQ ID NO:2). As indicated above, the inventors have determined that the above polypeptide fragments are antigenic regions of the DR5 protein.

The epitope-bearing peptides and polypeptides of the invention may be produced by any conventional means. Hougthen, R. A., "General Method for the Rapid Solid-Phase Synthesis of Large Numbers of Peptides: Specificity of Antigen-Antibody Interaction at the Level of Individual Amino Acids," *Proc. Natl. Acad. Sci. USA* 82:5131-5135 (1985). This "Simultaneous Multiple Peptide Synthesis (SMPS)" process is further described in U.S. Pat. No. 4,631,211 to Hougthen et al. (1986).

As one of skill in the art will appreciate, DR5 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric DR5 protein or protein fragment alone (Fountoulakis et al., *J Biochem* 270:3958-3964 (1995)).

Polypeptide Assays

The present invention also relates to diagnostic assays such as quantitative and diagnostic assays for detecting levels of DR5 protein, or the soluble form thereof, in cells and tissues, including determination of normal and abnormal levels. Thus, for instance, a diagnostic assay in accordance with the invention for detecting over-expression of DR5, or soluble form thereof, compared to normal control tissue samples may be used to detect the presence of tumors, for example. Assay techniques that can be used to determine levels of a protein, such as a DR5 protein of the present invention, or a soluble form thereof, in a sample derived from a host are well-known to those of skill in the art. Such assay methods include radioimmunoassays, competitive-binding assays, Western Blot analysis, and ELISA assays.

Assaying DR5 protein levels in a biological sample can occur using any art-known method. By "biological sample" is intended any biological sample obtained from an individual, cell line, tissue culture, or other source containing DR5 receptor protein or mRNA. Preferred for assaying DR5 protein levels in a biological sample are antibody-based techniques. For example, DR5 protein expression in tissues can be studied with classical immunohistological methods. (Jalkanen, M. et al., *J. Cell. Biol.* 101:976-985 (1985); Jalkanen, M. et al., *J. Cell. Biol.* 105:3087-3096 (1987)). Other antibody-based methods useful for detecting DR5 protein gene expression include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," *Symp. Quant. Biol.* 51:597-609 (1986), Cold Spring Harbor; Beutler, B., and Cerami, A., *Annu. Rev. Biochem.* 57:505-518 (1988); Old, L. J., *Sci. Am.* 258:59-75 (1988); Fiers, W., *FEBS Lett.* 285:199-224 (1991)). The TNF-family ligands induce such various cellular responses by binding to TNF-family receptors, including the DR5 of the present invention. Cells which express the DR5 polypeptide and are believed to have a potent cellular response to DR5 ligands include primary dendritic cells, endothelial tissue, spleen, chronic lymphocytic leukemia, and human thymus stromal cells. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis (programmed cell death) is a physiological mechanism involved in the deletion of peripheral T lymphocytes of the immune system, and its dysregulation can lead to a number of different pathogenic processes (Ameisen, J. C., *AIDS* 8:1197-1213 (1994); Krammer, P. H. et al., *Curr. Opin. Immunol.* 6:279-289 (1994)).

Diseases associated with increased cell survival, or the inhibition of apoptosis, include cancers (such as follicular lymphomas, carcinomas with p53 mutations, and hormone-dependent tumors, such as breast cancer, prostrate cancer, Kaposi's sarcoma and ovarian cancer); autoimmune disorders (such as systemic lupus erythematosus and immune-related glomerulonephritis rheumatoid arthritis) and viral infections (such as herpes viruses, pox viruses and adenoviruses), inflammation; graft vs. host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, in one aspect, the present invention is directed to a method for enhancing apoptosis induced by a TNF-family ligand, which involves administering to a cell which expresses the DR5 polypeptide an effective amount of DR5 ligand, analog or an agonist capable of increasing DR5 mediated signaling. Preferably, DR5 mediated signaling is increased to treat a disease wherein decreased apoptosis or decreased cytokine and adhesion molecule expression is exhibited. An agonist can include soluble forms of DR5 and monoclonal antibodies directed against the DR5 polypeptide.

In a further aspect, the present invention is directed to a method for inhibiting apoptosis induced by a TNF-family ligand, which involves administering to a cell which expresses the, DR5 polypeptide an effective amount of an antagonist capable of decreasing DR5 mediated signaling. Preferably, DR5 mediated signaling is decreased to treat a disease wherein increased apoptosis or NFkB expression is exhibited. An antagonist can include soluble forms of DR5 and monoclonal antibodies directed against the DR5 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular p H changes caused by receptor activation. For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds (antagonists) which inhibit activation of the receptor polypeptide of the present invention by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia, L. A., and Goeddel, D. V., *J. Biol. Chem.* 267:4304-4307 (1992). Thus, in a further aspect, a screening method is provided for determining whether a candidate agonist or antagonist is capable of enhancing or inhibiting a cellular response to a TNF-family ligand. The method involves contacting cells which express the DR5 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the DR5 polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonist s include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457-1458 (1995)). Further preferred agonist include polyclonal and monoclonal antibodies raised against the DR5 polypeptide, or a fragment thereof. Such agonist antibodies raised against a TNF-family receptor are disclosed in Tartaglia, L. A., et al., *Proc. Natl. Acad. Sci. USA* 88:9292-9296 (1991); and Tartaglia, L. A., and Goeddel, D. V., *J. Biol. Chem.* 267 (7):4304-4307 (1992) See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus E1B, Baculovirus p. 35 and IAP, Cowpox virus crmA, Epstein-Barr virus BHRF1, LMP-1, African swine fever virus LMW5-HL, and Herpesvirus y134.5), calpain inhibitors, cysteine protease inhibitors, and tumor promoters (such as PMA, Phenobarbital, and alpha-Hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the DR5 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the DR5 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding DR5, or fragments thereof, can be by any promoter known in the art to act in vertebrate, preferably human cells. Such promoters can be inducible or a constitutive. Such promoters include, but are not limited to, the SV40 early promoter region (Bernoist and Chambon, *Nature* 29:304-310 (1981), the promoter contained in the 3' long terminal repeat of Rous sarcoma virus (Yamamoto et al., *Cell* 22:787-797 (1980), the herpes thymidine promoter (Wagner et al., *Proc. Natl. Acad. Sci. U.S.A.* 78:1441-1445 (1981), the regulatory sequences of the metallothionein gene (Brinster, et al., *Nature* 296:39-42 (1982)), etc.

The antisense nucleic acids of the invention comprise a sequence complementary to at least a portion of an RNA transcript of a DR5 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded DR5 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a DR5RNA it may contain and still form a stable duplex (or triplex as the case may be). One skilled in the art can ascertain a tolerable degree of mismatch by use of standard procedures to determine the melting point of the hybridized complex.

Potential antagonists according to the invention also include catalytic RNA, or a ribozyme (See, e.g., PCT International Publication WO 90/11364, published Oct. 4, 1990; Sarver et al, *Science* 247:1222-1225 (1990). While ribozymes that cleave mRNA at site specific recognition sequences can be used to destroy DR5 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). There are numerous potential hammerhead ribozyme cleavage sites within the nucleotide sequence of DR5 (FIGS. 1A and 1B). Preferably, the ribozyme is engineered so that the cleavage recognition site is located near the 5' end of the DR5 mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Further antagonist according to the present invention include soluble forms of DR5, i.e., DR5 fragments that include the ligand binding domain from the extracellular region of the full length receptor. Such soluble forms of the receptor, which may be naturally occurring or synthetic, antagonize DR5 mediated signaling by competing with the cell surface DR5 for binding to TNF-family ligands. Thus, soluble forms of the receptor that include the ligand binding domain are novel cytokines capable of inhibiting apoptosis induced by TNF-family ligands. These may be expressed as monomers, but, are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (Hughes, D. P. and Crispe, I. N., *J. Exp. Med.* 182:1395-1401 (1995)).

The term "antibody" (Ab) or "monoclonal antibody" (mAb) as used herein is meant to include intact molecules as well as fragments thereof (such as, for example, Fab, and F(ab')$_2$ fragments) which are capable of binding an antigen. Fab, Fab', and F (ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

Antibodies according to the present invention may be prepared by any of a variety of standard methods using DR5 immunogens of the present invention. As indicated, such DR5 immunogens include the full length DR5 polypeptide (which may or may not include the leader sequence) and DR5 polypeptide fragments such as the ligand binding domain, the transmembrane domain, the intracellular domain and the death domain.

Antibodies of the invention can be used in methods known in the art relating to the localization and activity of the polypeptide sequences of the invention, e.g., for imaging these polypeptides, measuring levels thereof in appropriate physiological samples, etc. The antibodies also have use in immunoassays and in therapeutics as agonists and antagonists of DR5.

Proteins and other compounds which bind the DR5 domains are also candidate agonist and antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, J. et al., *Cell* 75:791-803 (1993); Zervos, A. S. et al., *Cell* 72:223-232 (1993)). Preferably, the yeast two-hybrid system is used according to the present invention to capture compounds which bind to either the DR5 ligand binding domain or to the DR5 intracellular domain. Such compounds are good candidate agonist and antagonist of the present invention.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, DR5 ligands, TRAIL, TNF-α, lymphotoxin-α (LT-α, also known as TNF-β), LT-β (found in complex heterotrimer LT-α2-β), FasL, CD40, CD27, CD30, 4-1BB, OX40 and nerve growth factor (NGF). An example of an assay that can be performed to determine the ability of DR5 and derivatives (including fragments) and analogs thereof to bind TRAIL is described below in Example 6.

Representative therapeutic applications of the present invention are discussed in-more detail below. The state of immunodeficiency that defines AIDS is secondary to a decrease in the number and function of CD4$^+$ T-lymphocytes. Recent reports estimate the daily loss of CD4$^+$ T cells to be between $3.5 \times 10^7$ and $2 \times 10^9$ cells (Wei X. et al., *Nature* 373: 117-122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., *AIDS* 8:1197-1213 (1994); Finkel, T. H., and Banda, N. K., *Curr. Opin. Immunol.* 6:605-615 (1995); Muro-Cacho, C. A. et al., *J. Immunol.* 154:5555-5566 (1995)). Furthermore, apoptosis and CD4$^+$ T-lymphocyte depletion is tightly correlated in different animal models of AIDS (Brunner, T., et al., *Nature* 373:441-444 (1995); Gougeon, M. L., et al., *AIDS Res. Hum. Retroviruses* 9:553-563 (1993)) and, apoptosis is not observed in those animal models in which viral replication does not result in AIDS (Gougeon, M. L. et al., *AIDS Res. Hum. Retroviruses* 9:553-563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., *J. Virol.* 70:199-206 (1996)). Further the TNF-family ligand was detectable in uninfected macrophages and its expression was upregulated following HIV infection resulting in selective killing of uninfected CD4 T-lymphocytes (Badley, A. D et al., *J. Virol.* 70:199-206 (1996)). Thus, by the invention, a method for treating HIV$^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence the immune system is already at the effector stage. Agonists of the present invention are able to suppress the immune response to both allografts and xenografts because lymphocytes activated and differentiated into effector cells will express the DR5 polypeptide, and thereby are susceptible to compounds which enhance apoptosis. Thus, the present invention further provides a method for creating immune privileged tissues.

DR5 antagonists may be useful for treating inflammatory diseases, such as rheumatoid arthritis, osteoarthritis, psoriasis, septicemia, and inflammatory bowel disease.

In addition, due to lymphoblast expression of DR5, soluble DR5 agonist or antagonist mABs may be used to treat this form of cancer. Further, soluble DR5 or neutralizing mABs may be used to treat various chronic and acute forms of inflammation such as rheumatoid arthritis, osteoarthritis, psoriasis, septicemia, and inflammatory bowel disease.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit DR5 mediated apoptosis. Of course, where it is desired for apoptosis is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients (i.e., carriers).

It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of DR5 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DR5 agonists or antagonists is typically administered at a dose rate of about 1 μg/kg/hour to about 50 μg/kg/hour, either by 1-4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions are provided comprising an agonist or antagonist (including DR5 polynucleotides and polypeptides of the invention) and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and a TNF-family ligand, clinical side effects can be reduced by using lower doses of both the ligand and the agonist. It will be understood that the agonist can be "co-administered" either before, after, or simultaneously with the TNF-family ligand, depending on the exigencies of a particular therapeutic application. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like.

Water is a preferred carrier when the pharmaceutical composition is administered intravenously. Saline solutions and aqueous dextrose and glyceral solutions can be employed as liquid carriers, particularly for injectable solutions.

The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble DR5 polypeptides, DR5 polypeptide containing the transmembrane region can also be used when appropriately solubilized by including detergents, such as CHAPS or NP-40, with buffer.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA and/or polynucleotides herein disclosed is used to clone genomic DNA of a DR5 gene. This can be accomplished using a variety of well known techniques and libraries, which generally are available commercially. The genomic DNA is then used for in situ chromosome mapping using well known techniques for this purpose.

In addition, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60 bp. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

Example 1

Expression and Purification in *E. coli*

The DNA sequence encoding the mature DR5 protein in the deposited cDNA clone (ATCC No. 97920) is amplified using PCR oligonucleotide primers specific to the amino terminal sequences of the DR5 protein and to vector sequences 3' to the gene. Additional nucleotides containing restriction sites to facilitate cloning are added to the 5' and 3' sequences respectively.

The following primers are used for expression of DR5 extracellular domain in *E. coli*: The 5' primer has the sequence 5'-CGCCCATGGAGTCT GCTCTGATCAC-3' (SEQ ID NO:8) and contains the underlined NcoI site; and the 3' primer has the sequence 5'-CGC AAGCTTTTAGCCTGATTC TTTGTGGAC-3' (SEQ ID NO:9) and contains the underlined HindIII site.

The restriction sites are convenient to restriction enzyme sites in the bacterial expression vector pQE60, which are used for bacterial expression in this example. (Qiagen, Inc. 9259 Eton Avenue, Chatsworth, Calif., 91311). pQE60 encodes ampicillin antibiotic resistance ("Amp'") and contains a bacterial origin of replication ("ori"), an IPTG inducible promoter, and a ribosome binding site ("RBS").

The amplified DR5DNA and the vector pQE60 both are digested with NcoI and HindIII and the digested DNAs are then ligated together. Insertion of the DR5 protein DNA into the restricted pQE60 vector places the DR5 protein coding region downstream of and operably linked to the vector's IPTG-inducible promoter and in-frame with an initiating AUG appropriately positioned for translation of DR5 protein.

The ligation mixture is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan'"), is used in carrying out the illustrative example described herein. This strain, which is only one of many that are suitable for expressing DR5 protein, is available commercially from Qiagen, supra.

Transformants are identified by their ability to grow on LB plates in the presence of ampicillin and kanamycin. Plasmid DNA is isolated from resistant colonies and the identity of the cloned DNA confirmed by restriction analysis, PCR, and DNA sequencing.

Clones containing the desired constructs are grown overnight ("O/N") in liquid culture in LB media supplemented with both ampicillin (100 µg/ml) and kanamycin (25 µg/ml). The 0/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lad repressor. Cells subsequently are incubated further for 3 to 4 hours.

Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2X phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2X PBS at a concentration of 95 µ/ml.

Example 2

Expression in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g. the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC67109). Mammalian host cells that could be used include, human Hela 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene of interest can be expressed in stable cell lines that contain the gene integrated into a chromosome. Co-transfection with a selectable marker such as dhfr, gpt, neomycin, hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem.* 227:277-279 (1991); Bebbington et al., *Bio/Technology* 10:169-175 (1992)). Using these markers, the mammalian cells are grown in selective medium and the cells with the highest resistance selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 5:438-447 (March 1985)), plus a fragment of the CMV-enhancer (Boshart et al., *Cell* 41:521-530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of the DR5 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids, can be selected by growing the cells in a selective medium (alpha minus MEM, Life Technologies) supplemented with the chemotherapeutic agent methotrexate (MTX). The amplification of the DHFR genes in cells resistant to methotrexate (MTX) has been well documented (see, e.g., Alt, F. W., Kellems, R. M., Bertino, J. R., and Schimke, R. T., *J. Biol. Chem.* 253:

1357-1370 (1978); Hamlin, J. L. and Ma, C., *Biochem. et Biophys. Acta* 1097:107-143 (1990); Page, M. J. and Sydenham, M. A. 1991, *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains, for expressing the gene of interest, the strong promoter of the long terminal repeat (LTR) of the Rous Sarcoma Virus (Cullen et al., *Molecular and Cellular Biology* 5:438-447(March 1985), plus a fragment isolated from the enhancer of the immediate early gene of human cytomegalovirus (CMV) (Boshart et al., *Cell* 41:521-530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the DR5 polypeptide in a regulated way in mammalian cells (Gossen, M., & Bujard, H., *Proc. Natl. Acad. Sci. USA* 89:5547-5551 (1992). For the polyadenylation of the mRNA, other signals, e.g., from the human growth hormone or globin genes, can be used as well.

Stable cell lines carrying a gene of interest integrated into the chromosomes can also be selected upon co-transfection with a selectable marker such as gpt, G418, or hygromycin. It is advantageous to use more than one selectable marker in the beginning, e.g., G418 plus methotrexate.

The plasmid pC4 is digested with the restriction enzyme BamHI and then dephosphorylated using calf intestinal phosphates by procedures known in the art. The vector is then isolated from a 1% agarose gel.

The DNA sequence encoding the complete polypeptide is amplified using PCR oligonucleotide primers corresponding to the 5' and 3' sequences of the desired portion of the gene. The 5' primer containing the underlined BamHI site, a Kozak sequence, and an AUG start codon, has the following sequence: 5'-CGC<u>GGATCC</u>GCCATCATGGAACAACGGGGACAGAAC-3' (SEQ ID NO:10). The 3' primer, containing the underlined Asp718 site, has the following sequence: 5'-CGC<u>GGTACC</u>TTAGGACATGGCAGAGTC-3' (SEQ ID NO:11).

The amplified fragment is digested with the endonuclease BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using the lipofectin method (Feigner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reversed phase HPLC analysis.

Cloning and Expression in COS Cells

The expression plasmid, pDR5—HA, is made by cloning a cDNA encoding the soluble extracellular domain of the DR5 protein into the expression vector pcDNAI/Amp or pcDNAIII (which can be obtained from Invitrogen, Inc.). The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 and a polyadenylation signal arranged so that a cDNA can be conveniently placed under expression control of the CMV promoter and operably linked to the SV40 intron and the polyadenylation signal by means of restriction sites in the polylinker. A DNA fragment encoding the extracelluar domain of the DR5 polypeptide and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope.

The plasmid construction strategy is as follows. The DR5 cDNA of the deposited clone is amplified using primers that contain convenient restriction sites, much as described above for construction of vectors for expression of DR5 in *E coli*. To facilitate detection, purification and characterization of the expressed DR5, one of the primers contains a hemagglutinin tag ("HA tag") as described above.

Suitable primers include the following, which are used in this example. The 5' primer, containing the underlined BamHI site has the following sequence: 5'-CGC<u>GGATCC</u>GCCATCATGGAACAACGGGGACAGAAC-3' (SEQ ID NO:10). The 3' primer, containing the underlined Asp718 restriction sequence has the following sequence: 5'-CGC<u>GGTACC</u>TTAGCCTGATTCTTTTGGAC-3' (SEQ ID NO:12).

The PCR amplified DNA fragment and the vector, pcDNAI/Amp, are digested with BamHI and Asp718 and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the extracellular domain of the DR5 polypeptide For expression of recombinant DR5, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of DR5 by the vector.

Expression of the DR5—HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al., cited above. Proteins are precipitated from the cell lysate and from the culture media using an HA-specific monoclonal antibody. The precipitated proteins then are analyzed by SDS-PAGE and autoradiography. An expression product of the expected size is seen in the cell to lysate, which is not seen in negative controls.

The primer sets used for expression in this example are compatible with pC4 used for CHO expression in this example, pcDNAI/Amp for COS expression in this example, and pA2 used for baculovirus expression in the following example. Thus, for example, the complete DR5 encoding fragment amplified for CHO expression could also be ligated into pcDNAI/Amp for COS expression or pA2 for baculovirus expression.

Example 3

Cloning and Expression of the Soluble Extracellular Domain of DR5 in a Baculovirus Expression System In this illustrative example, the plasmid shuttle vector pA2 is used to insert the cloned DNA encoding the complete protein, including its naturally associated signal sequence, into a baculovirus to express the DR5 protein, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedron promoter of the Autograph californica nuclear polyhedrosis virus (ACMNPV) followed by convenient restriction sites. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide. Many other baculovirus vectors could be used in place of pA2, such as pAc373, pVL941 and pAcIM1 provided, as one skilled in the art would readily appreciate, that construction provides appropriately located signals for transcription, translation, secretion, and the like, such as an in-frame AUG and a signal peptide, as required. Such vectors are described, for example, in Luckow et al., *Virology* 170:31-39 (1989).

The cDNA sequence encoding the soluble extracellular domain of DR5 protein in the deposited clone (ATCC No. 97920) is amplified using PCR oligonucleotide primers corresponding to the 5' and 3' sequences of the gene:

The 5' primer for DR5 has the sequence 5'-CGC GGATCCGCCATCATGGA ACAACGGGGACAGAAC-3' (SEQ ID NO:10) containing the underlined BamHI restriction enzyme site. Inserted into an expression vector, as described below, the 5' end of the amplified fragment encoding DR5 provides an efficient cleavage signal peptide. An efficient signal for initiation of translation in eukaryotic cells, as described by Kozak, M., *J. Mol. Biol.* 196:947-950 (1987) is appropriately located in the vector portion of the construct.

The 3' primer for DR5 has the sequence 5'-CGC GGTACCTTAGCCT GATTCTTTGTGGAC-3' (SEQ ID NO:12) containing the underlined Asp718 restriction followed by nucleotides complementary to the DR5 nucleotide sequence in FIGS. 1A and 1B, followed by the stop codon.

The amplified fragment is isolated from a 1% agarose gel using a commercially available kit ("Geneclean," BIO 101 Inc., La Jolla, Calif.) The fragment then is digested with BamHI and Asp718 and again is purified on a 1% agarose gel. This fragment is designated "F1."

The plasmid is digested with the restriction enzymes Bam HI and Asp718 and optionally can be dephosphorylated using calf intestinal phosphatase, using routine procedures known in the art. The DNA is then isolated from a 1% agarose gel using a commercially available kit ("Geneclean" BIO 101 Inc., La Jolla, Calif.). The vector DNA is designated herein "V1."

Fragment F1 and the dephosphorylated plasmid V1 are ligated together with T4 DNA ligase. *E. coli* HB101 cells, or other suitable *E. coli* hosts such as XL-1 Blue (Stratagene Cloning Systems, La Jolla, Calif.) cells, are transformed with the ligation mixture and spread on culture plates. Bacteria are identified that contain the plasmid with the human DR5 using the PCR method, in which one of the primers that is used to amplify the gene and the second primer is from well within the vector so that only those bacterial colonies containing the DR5 gene fragment will show amplification of the DNA. The sequence of the cloned fragment is confirmed by DNA sequencing. This plasmid is designated herein pBac DR5.

5 µg of the plasmid pBac DR5 is co-transfected with 1.0 µg of a commercially available linearized baculovirus DNA ("BaculoGold™ baculovirus DNA", Pharmingen, San Diego, Calif.), using the lipofectin method described by Feigner et al., *Proc. Natl. Acad. Sci. USA* 84:7413-7417 (1987). 1 µg of BaculoGold™ virus DNA and 5 µg of the plasmid pBac DR5 are mixed in a sterile well of a microliter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours, the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, cited above. An agarose gel with "Blue Gal" (Life Technologies Inc., Gaithersburg, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Md., pages 9-10). After appropriate incubation, blue stained plaques are picked with the tip of a micropipettor (e.g, Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later, the supernatants of these culture dishes are harvested and then they are stored at 4° C. The recombinant virus is called V-DR5.

To verify expression of the DR5 gene, Sf9 cells are grown in Grace's medium supplemented with 10% heat-inactivated FBS. The cells are infected with the recombinant baculovirus V-DR5 at a multiplicity of infection ("MOI") of about 2 (about 1 to about 3). Six hours later, the medium is removed and is replaced with SF900 II medium minus methionine and cysteine (available from Life Technologies Inc., Gaithersburg, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 4

Tissue Distribution of DR5 Gene Expression

Northern blot analysis was carried out to examine DR5 gene expression in human tissues, using methods described by, among others, Sambrook et al., cited above. A cDNA probe containing the entire nucleotide sequence of the DR5 protein (SEQ ID NO:1) was labeled with $^{32}$P using the Rediprime™ DNA labeling system (Amersham Life Science), according to manufacturer's instructions. After labeling, the probe was purified using a CHROMA SPIN100™ column (Clontech Laboratories, Inc.), according to manufacturer's protocol number PT1200-1. The purified labeled probe was then used to examine various human tissues for DR5 mRNA.

Multiple Tissue Northern (MTN) blots containing various human tissues (H) or human immune system tissues (IM) were obtained from Clontech (Palo Alto, Calif.) and examined with labeled probe using ExpressHyb™ hybridization solution (Clontech) according to manufacturer's protocol number PT1190-1. Following hybridization and washing, the blots were mounted and exposed to film at -70° C. overnight. The films were developed according to standard procedures. Expression of DR5 was detected in heart, brain, placenta, lung, liver, skeletal muscle, kidney, pancreas, spleen, thymus, prostate, testis, uterus, small intestine, colon, peripheral blood leukocytes (PBLs), lymph node, bone marrow, and fetal liver.

Expression of DR5 was also assessed by Northern blot in the following cancer cell lines, HL60 (promyelocytic leukemia), Hela cell S3, K562 (chronic myelogeneous leukemia), MOLT4 (lymphoblast leukemia), Raji (Burkitt's lymphoma), SW480 (colorectal adenocarcinoma), A549 (lung carcinoma), and G361 (melanoma), and was detected in all of the cell lines tested.

Example 5

DR5 Induced Apoptosis in Mammalian Cells

Overexpression of Fas/APO-1 and TNFR-1 in mammalian cells mimics receptor activation (M. Muzio et al., Cell 85: 817-827 (1996); M. P. Boldin et al., Cell 85:803-815 (1996)). Thus, this system was utilized to study the functional role of DR5 in inducing apoptosis. This example demonstrates that overexpression of DR5 induced apoptosis in both MCF7 human breast carcinoma cells and in human epitheloid carcinoma (Hela)) cells.

Experimental Design

Cell death assays were performed essentially as previously described (A. M. Chinnaiyan, et al., Cell 81:505-12 (1995); M. P. Boldin, et al., J Biol Chem 270: 7795-8 (1995); F. C. Kischkel, et al., EMBO 14:5579-5588 (1995); A. M. Chinnaiyan, et al., J Biol Chem 271: 4961-4965 (1996)). Briefly, MCF-7 human breast carcinoma clonal cell lines and Hela cells were co-transfected with vector, DR5, DR5A (52-411), or TNFR-1, together with a beta-galactosidase reporter construct.

MCF7 and Hela cells were transfected using the lipofectamine procedure (GIBCO-BRL), according to the manufacturer's instructions. 293 cells were transfected using $CaPO_4$ precipitation. Twenty-four hours following transfection, cells were fixed and stained with X-Gal as previously described (A. M. Chinnaiyan, et al., Cell 81:505-12 (1995); M. P. Boldin, et al., J Biol Chem 270:7795-8 (1995); F. C. Kischkel, et al., EMBO 14:5579-5588 (1995)), and examined microscopically. The data (mean±SD) presented in FIG. 5 represents the percentage of round, apoptotic cells as a function of total beta-galactosidase positive cells (n=3). Overexpression of DR5 induced apoptosis in both MCF7 (FIG. 5A) and Hela cells (FIG. 5B).

MCF7 cells were also transfected with a DR5 expression construct in the presence of z-VAD-fmk (20 µl) (Enzyme Systems Products, Dublin, Calif.) or co-transfected with a three-fold excess of CrmA (M. Tewari et al., J Biol Chem 270:3255-60 (1995)), or FADD-DN expression construct, or vector alone. The data presented in FIG. 5C shows that apoptosis induced by DR5 was attenuated by caspase inhibitors, but not by dominant negative FADD.

As depicted in FIG. 5D, DR5 did not associate with FADD or TRADD in vivo. 293 cells were co-transfected with the indicated expression constructs using calcium phosphate precipitation. After transfection (at 40 hours), cell lysates were prepared and immunoprecipitated with Flag M2 antibody affinity gel (IBI, Kodak), and the presence of FADD or myc-tagged TRADD (myc-TRADD) was detected by immunoblotting with polyclonal antibody to FADD or horseradish peroxidase (HRP) conjugated antibody to myc (BMB) (Baker, S. J. et al., Oncogene 12:1 (1996); Chinnaiyan, A. M. et al., Science 274:990 (1996)).

Figure 5E:
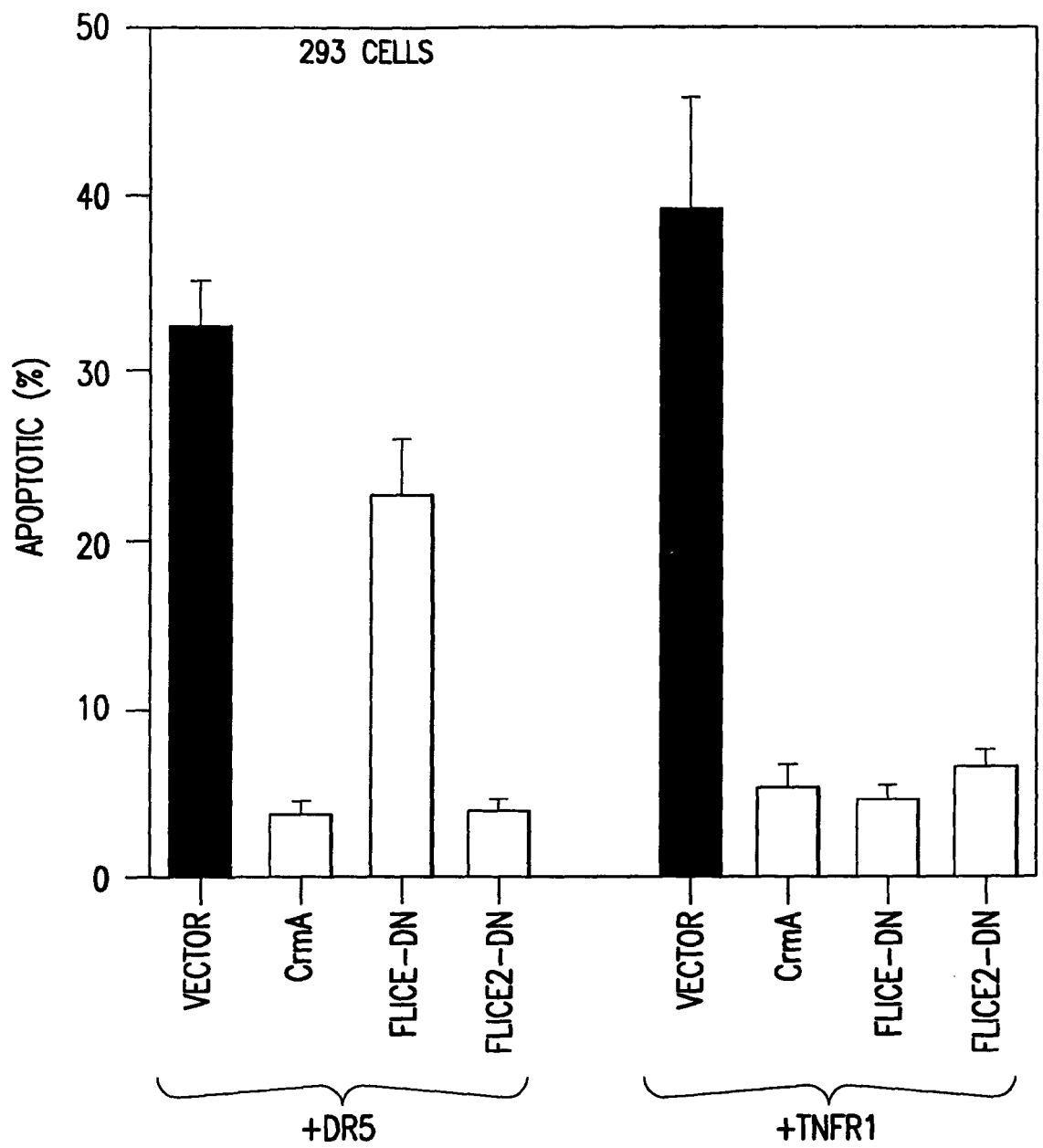
FIG. 5E is a bar graph showing that a dominant negative version of a newly identified FLICE-like molecule, FLICE2 (Vincenz, C. et al., *J. Biol. Chem.* 272:6578 (1997)), efficiently blocked DR5-induced apoptosis, while dominant negative FLICE had only partial effect under conditions it blocked. It also shows that TNFR-1 blocked apoptosis effectively.

As depicted in FIG. 5E, FLICE 2-DN blocks DR5-induced apoptosis. 293 cells were co-transfected with DR5 or TNFR-1 expression construct and a fourfold excess of CrmA, FLICE-DN, FLICE 2-DN, or vector alone in the presence of a beta-galactosidase reported construct as indicated. Cells were stained and examined 25-30 hours later.

Results

Overexpression of DR5, induced apoptosis in both MCF7 human breast carcinoma cells (FIG. 5A) and in human epitheloid carcinoma (Hela) cells (FIG. 5B). Most of the transfected cells displayed morphological changes characteristic of cells undergoing apoptosis (Earnshaw, W. C., *Curr. Biol.* 7:337 (1995)), becoming rounded, condensed and detaching from the dish. Deletion of the death domain abolished killing ability. Like DR4, DR5-induced apoptosis was blocked by caspase inhibitors, CrmA and z-VAD-fmk, but dominant negative FADD was without effect (FIG. 5C). Consistent with this, DR5 did not interact with FADD and TRADD in vivo (FIG. 5D). A dominant negative version of a newly identified FLICE-like molecule, FLICE2 (Vincenz, C. et al., *J. Biol. Chem.* 272:6578 (1997)), efficiently blocked DR5-induced apoptosis, while dominant negative FLICE had only partial effect under conditions it blocked. TNFR-1 induced apoptosis effectively (FIG. 5E). Taken together, the evidence suggests that DR5 engages an apoptotic program that involves activation of FLICE2 and downstream caspases, but is independent of FADD.

Example 6

The Extracellular Domain of DR5 Binds the Cytotoxic Ligand-TRAIL, and Blocks TRAIL-Induced Apoptosis As discussed above, TRAIL/Apo2L is a cytotoxic ligand that belongs to the tumor necrosis factor (TNF) ligand family and induces rapid cell death of many transformed cell lines, but not normal tissues, despite its death domain containing receptor, DR4, being expressed on both cell types. This example shows that the present receptor, DR5, also binds TRAIL.

Given the similarity of the extracellular ligand binding cysteine-rich domains of DR5 and DR4, the present inventors theorized that DR5 would also bind TRAIL. To confirm this, the soluble extracellular ligand binding domains of DR5 were expressed as fusions to the Fc portion of human immunoglobulin (IgG).

Figure 6A:
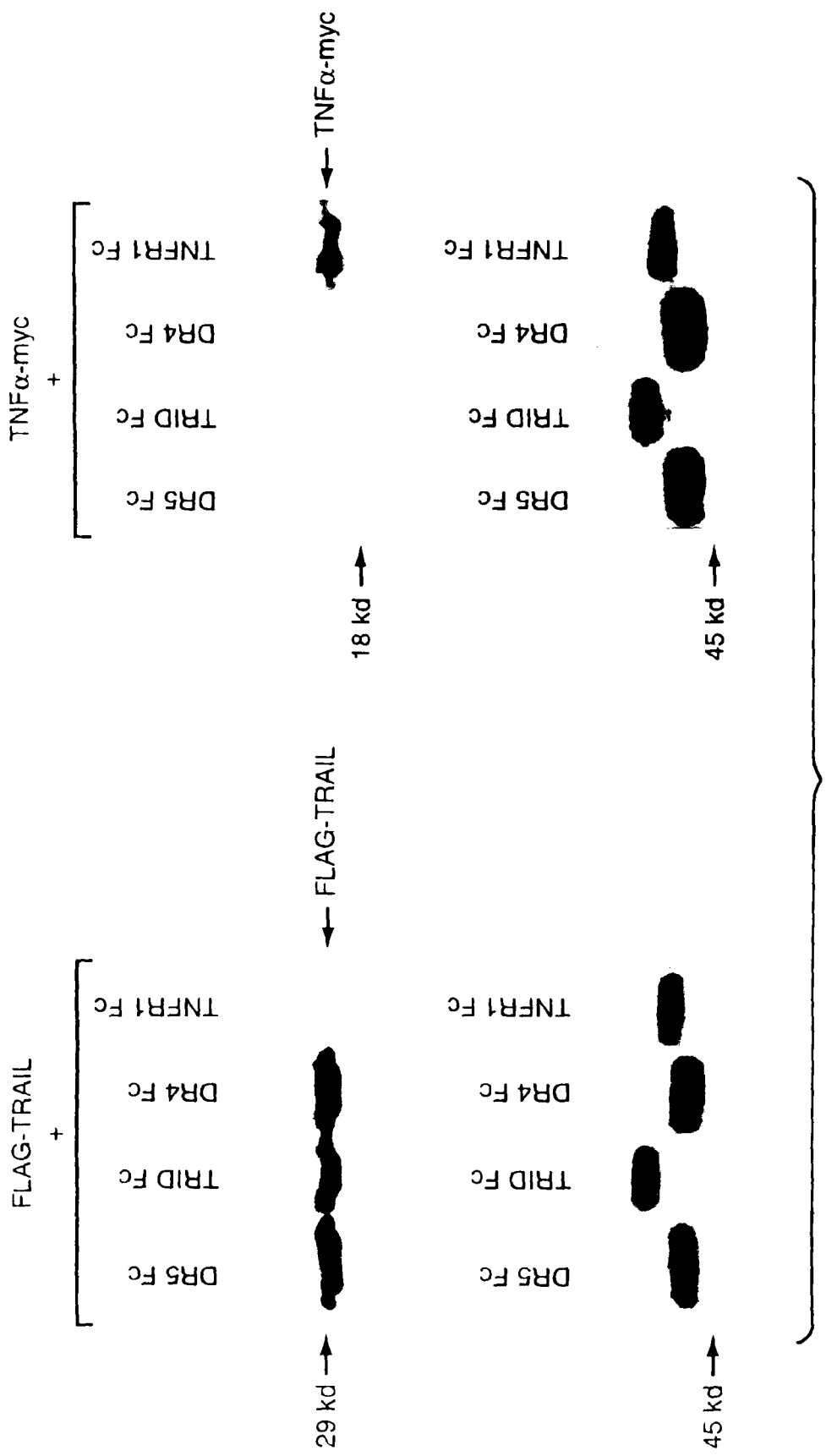
FIG. 6A is an immunoblot showing that DR5-Fc (as well as DR4 and TRID) specifically bound TRAIL, but not the related cytotoxic ligand TNFα. The bottom panel of FIG. 6A shows the input Fc-fusions present in the binding assays.

As shown in FIG. 6A, DR5-Fc specifically bound TRAIL, but not the related cytotoxic ligand TNFα. In this experiment, the Fc-extracellular domains of DR5, DR4, TRID, or TNFR1 and the corresponding ligands were prepared and binding assays performed as described in Pan et al., *Science* 276:111 (1997). The respective Fc-fusions were precipitated with protein G-Sepharose and co-precipitated soluble ligands were detected by immunoblotting with anti-Flag (Babco) or anti-myc-HRP (BMB). The bottom panel of FIG. 6A shows the input Fc-fusions present in the binding assays.

Figure 6C:
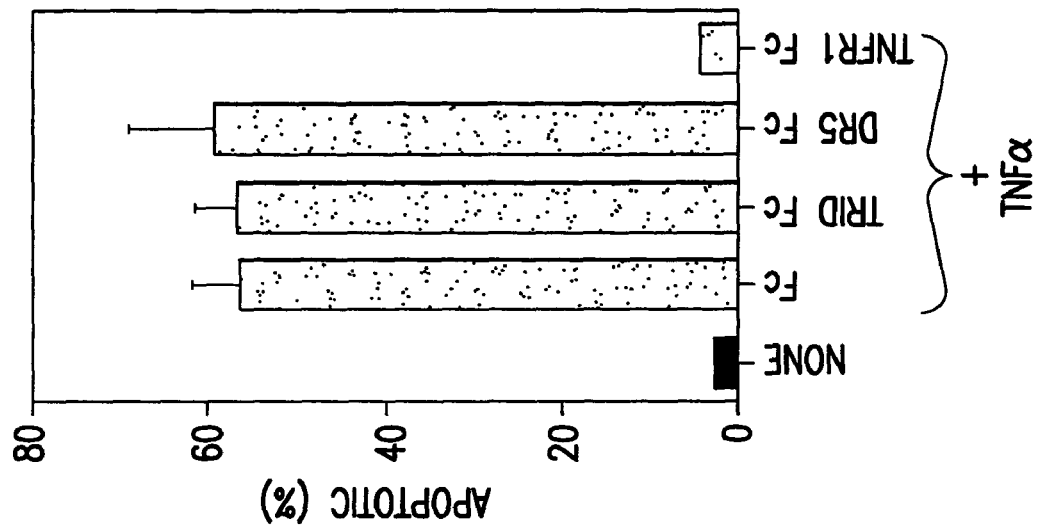
FIG. 6C is a bar graph showing that DR5-Fc had no effect on apoptosis TNFα-induced cell death under conditions where TNFR1-Fc completely abolished TNFα killing.
Figure 6B:
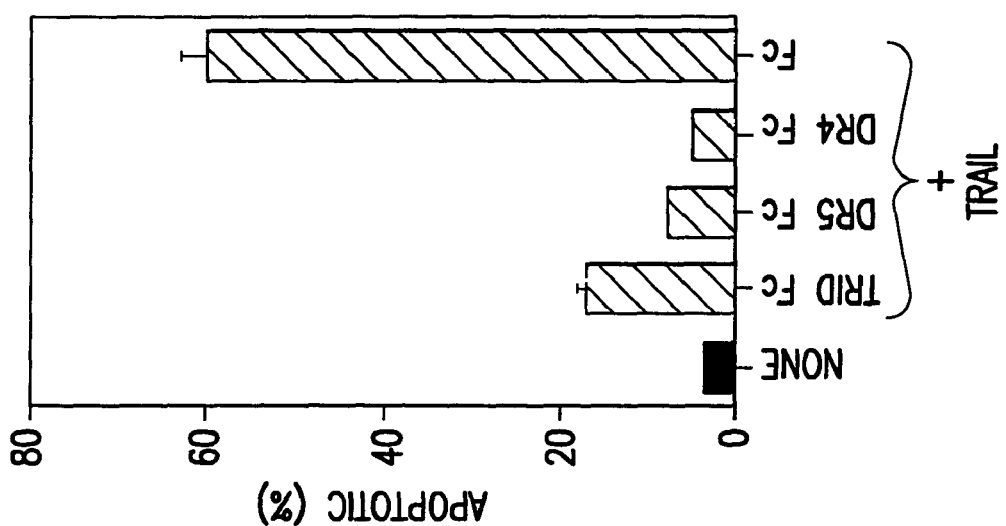
FIG. 6B is a bar graph showing that DR5-Fc blocked the ability of TRAIL to induce apoptosis. The data (mean±SD) shown in FIG. 6B are the percentage of apoptotic nuclei among total nuclei counted (n=4).

Additionally, DR5-Fc blocked the ability of TRAIL to induce apoptosis (FIG. 6B). MCF7 cells were treated with soluble TRAIL (200 ng/ml) in the presence of equal amounts of Fc-fusions or Fc alone. Six hours later, cells were fixed and examined as described in Pan et al., Id. The data (mean±SD) shown in FIG. 6B are the percentage of apoptotic nuclei among total nuclei counted (n=4).

Finally, DR5-Fc had no effect on apoptosis TNFα-induced cell death under conditions where TNFR1-Fc completely abolished TNFα killing (FIG. 6C). MCF7 cells were treated with TNFα (40 ng/ml; Genentech, Inc.) in the presence of equal amounts of Fc-fusions or Fc alone. Nuclei were stained and examined 11-15 hours later.

The new identification of DR5 as a receptor for TRAIL adds further complexity to the biology of TRAIL-initiated signal transduction.

It will be clear that the invention may be practiced otherwise than as particularly described in the foregoing description and examples.

Numerous modifications and variations of the present invention are possible in light of the above teachings and, therefore, are within the scope of the appended claims.

The entire disclosures of all patents, patent applications, and publications referred to herein are hereby incorporated by reference.

What is claimed is:

1. An isolated polynucleotide comprising a nucleic acid which encodes amino acids 1 to 360 of SEQ ID NO:2.

2. The polynucleotide of claim 1, which comprises nucleotides 283 to 1362 of SEQ ID NO:1.

3. The polynucleotide of claim 1, wherein said nucleic acid encodes amino acids −50 to 360 of SEQ ID NO:2.

4. The polynucleotide of claim 3, which comprises nucleotides 133 to 1362 of SEQ ID NO:1.

5. The polynucleotide of claim 4, which comprises nucleotides 130 to 1362 of SEQ ID NO:1.

6. The polynucleotide of claim 1, which encodes a polypeptide which binds TRAIL.

7. The polynucleotide of claim 1, which encodes a polypeptide which induces apoptosis.

8. The polynucleotide of claim 1, further comprising a heterologous polynucleotide.

9. The polynucleotide of claim 8, wherein said heterologous polynucleotide encodes a heterologous polypeptide.

10. The polynucleotide of claim 9, wherein said heterologous polypeptide comprises an immunoglobulin Fc region.

11. The polynucleotide of claim 10, wherein said immunoglobulin Fc region is a human immunoglobulin Fc region.

12. A method of producing a vector that comprises inserting the polynucleotide of claim 1 into a vector.

13. A vector comprising the polynucleotide of claim 1.

14. The vector of claim 13, wherein said polynucleotide is operably associated with a heterologous regulatory sequence.

15. A host cell comprising the polynucleotide of claim 1.

16. The host cell of claim 15, wherein said polynucleotide is operably associated with a heterologous regulatory sequence.

17. A host cell comprising the polynucleotide of claim 6.

18. The host cell of claim 17, wherein said polynucleotide is operably associated with a heterologous regulatory sequence.

19. A method of producing the polypeptide encoded by the polynucleotide of claim 6, comprising culturing a host cell comprising said polynucleotide under conditions such that said polypeptide is expressed, and recovering said polypeptide.

20. An isolated polynucleotide comprising a nucleic acid which encodes the mature amino acid sequence encoded by the cDNA clone in ATCC Deposit No. 97920.

21. The polynucleotide of claim 20, wherein said nucleic acid encodes the complete amino acid sequence encoded by the cDNA clone in ATCC Deposit No. 97920.

22. The polynucleotide of claim 20, wherein said nucleic acid encodes a polypeptide which binds TRAIL.

23. The polynucleotide of claim 20, wherein said nucleic acid encodes a polypeptide which induces apoptosis.

24. The polynucleotide of claim 20, further comprising a heterologous polynucleotide.

25. The polynucleotide of claim 24, wherein said heterologous polynucleotide encodes a heterologous polypeptide.

26. The polynucleotide of claim 25, wherein said heterologous polypeptide comprises an immunoglobulin Fc region.

27. The polynucleotide of claim 26, wherein said immunoglobulin Fc region is a human immunoglobulin Fc region.

28. A method of producing a vector that comprises inserting the polynucleotide of claim 20 into a vector.

29. A vector comprising the polynucleotide of claim 20.

30. The vector of claim 29, wherein said polynucleotide is operably associated with a heterologous regulatory sequence.

31. A host cell comprising the polynucleotide of claim 20.

32. The host cell of claim 31, wherein said polynucleotide is operably associated with a heterologous regulatory sequence.

33. A host cell comprising the polynucleotide of claim 22.

34. The host cell of claim 33, wherein said polynucleotide is operably associated with a heterologous regulatory sequence.

35. A method of producing the polypeptide encoded by the polynucleotide of claim 20 comprising culturing a host cell comprising said polynucleotide under conditions such that said polypeptide is expressed, and recovering said polypeptide.

36. An isolated polynucleotide which encodes amino acids 1 to 133 of SEQ ID NO:2.

37. The polynucleotide of claim 36, which comprises nucleotides 283 to 681 of SEQ ID NO:1.

38. The polynucleotide of claim 36, wherein said nucleic acid encodes a polypeptide which binds TRAIL.

39. The polynucleotide of claim 36, further comprising a heterologous polynucleotide.

40. The polynucleotide of claim 39, wherein said heterologous polynucleotide encodes a heterologous polypeptide.

41. The polynucleotide of claim 40, wherein said heterologous polypeptide comprises an immunoglobulin Fc region.

42. The polynucleotide of claim 41, wherein said immunoglobulin Fc region is a human immunoglobulin Fc region.

43. A method of producing a vector that comprises inserting the polynucleotide of claim 36 into a vector.

44. A vector comprising the polynucleotide of claim 36.

45. The vector of claim 44, wherein said polynucleotide is operably associated with a heterologous regulatory sequence.

46. A host cell comprising the polynucleotide of claim 36.

47. The host cell of claim 46, wherein said polynucleotide is operably associated with a heterologous regulatory sequence.

48. A host cell comprising the polynucleotide of claim 38.

49. The host cell of claim 48, wherein said polynucleotide is operably associated with a heterologous regulatory sequence.

50. A method of producing a polypeptide comprising the amino acids encoded by the polynucleotide of claim 36, comprising culturing a host cell comprising said polynucleotide under conditions such that said polypeptide is expressed, and recovering said polypeptide.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1600 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: sig_peptide
      (B) LOCATION: 130..283

(ix) FEATURE:
      (A) NAME/KEY: CDS
      (B) LOCATION: 130..1362

(ix) FEATURE:
      (A) NAME/KEY: mat_peptide
      (B) LOCATION: 284..1362

(xi) SEQUENCE DESCRIPTION: SEQ ID NO:1:

```
CACGCGTCCG CGGGCGCGGC CGGAGAACCC CGCAATCTTT GCGCCCACAA AATACACCGA    60

CGATGCCCGA TCTACTTTAA GGGCTGAAAC CCACGGGCCT GAGAGACTAT AAGAGCGTTC   120

CCTACCGCC ATG GAA CAA CGG GGA CAG AAC GCC CCG GCC GCT TCG GGG       168
          Met Glu Gln Arg Gly Gln Asn Ala Pro Ala Ala Ser Gly
          -51 -50             -45                 -40

GCC CGG AAA AGG CAC GGC CCA GGA CCC AGG GAG GCG CGG GGA GCC AGG     216
Ala Arg Lys Arg His Gly Pro Gly Pro Arg Glu Ala Arg Gly Ala Arg
            -35             -30                 -25

CCT GGG CCC CGG GTC CCC AAG ACC CTT GTG CTC GTT GTC GCC GCG GTC     264
Pro Gly Pro Arg Val Pro Lys Thr Leu Val Leu Val Val Ala Ala Val
-20              -15                 -10

CTG CTG TTG GTC TCA GCT GAG TCT GCT CTG ATC ACC CAA CAA GAC CTA     312
Leu Leu Leu Val Ser Ala Glu Ser Ala Leu Ile Thr Gln Gln Asp Leu
     -5               1                 5                      10

GCT CCC CAG CAG AGA GCG GCC CCA CAA CAA AAG AGG TCC AGC CCC TCA     360
Ala Pro Gln Gln Arg Ala Ala Pro Gln Gln Lys Arg Ser Ser Pro Ser
             15                  20                 25

GAG GGA TTG TGT CCA CCT GGA CAC CAT ATC TCA GAA GAC GGT AGA GAT     408
Glu Gly Leu Cys Pro Pro Gly His His Ile Ser Glu Asp Gly Arg Asp
             30                  35                 40

TGC ATC TCC TGC AAA TAT GGA CAG GAC TAT AGC ACT CAC TGG AAT GAC     456
Cys Ile Ser Cys Lys Tyr Gly Gln Asp Tyr Ser Thr His Trp Asn Asp
             45                  50                 55

CTC CTT TTC TGC TTG CGC TGC ACC AGG TGT GAT TCA GGT GAA GTG GAG     504
Leu Leu Phe Cys Leu Arg Cys Thr Arg Cys Asp Ser Gly Glu Val Glu
             60                  65                 70

CTA AGT CCC TGC ACC ACG ACC AGA AAC ACA GTG TGT CAG TGC GAA GAA     552
Leu Ser Pro Cys Thr Thr Thr Arg Asn Thr Val Cys Gln Cys Glu Glu
75               80                  85                 90

GGC ACC TTC CGG GAA GAA GAT TCT CCT GAG ATG TGC CGG AAG TGC CGC     600
Gly Thr Phe Arg Glu Glu Asp Ser Pro Glu Met Cys Arg Lys Cys Arg
             95                  100                105

ACA GGG TGT CCC AGA GGG ATG GTC AAG GTC GGT GAT TGT ACA CCC TGG     648
Thr Gly Cys Pro Arg Gly Met Val Lys Val Gly Asp Cys Thr Pro Trp
             110                 115                120

AGT GAC ATC GAA TGT GTC CAC AAA GAA TCA GGC ATC ATC ATA GGA GTC     696
Ser Asp Ile Glu Cys Val His Lys Glu Ser Gly Ile Ile Ile Gly Val
             125                 130                135

ACA GTT GCA GCC GTA GTC TTG ATT GTG GCT GTG TTT GTT TGC AAG TCT     744
Thr Val Ala Ala Val Val Leu Ile Val Ala Val Phe Val Cys Lys Ser
     140                 145                 150

TTA CTG TGG AAG AAA GTC CTT CCT TAC CTG AAA GGC ATC TGC TCA GGT     792
Leu Leu Trp Lys Lys Val Leu Pro Tyr Leu Lys Gly Ile Cys Ser Gly
155                  160                 165                170

GGT GGT GGG GAC CCT GAG CGT GTG GAC AGA AGC TCA CAA CGA CCT GGG     840
Gly Gly Gly Asp Pro Glu Arg Val Asp Arg Ser Ser Gln Arg Pro Gly
             175                 180                185

GCT GAG GAC AAT GTC CTC AAT GAG ATC GTG AGT ATC TTG CAG CCC ACC     888
Ala Glu Asp Asn Val Leu Asn Glu Ile Val Ser Ile Leu Gln Pro Thr
             190                 195                200

CAG GTC CCT GAG CAG GAA ATG GAA GTC CAG GAG CCA GCA GAG CCA ACA     936
Gln Val Pro Glu Gln Glu Met Glu Val Gln Glu Pro Ala Glu Pro Thr
             205                 210                215

GGT GTC AAC ATG TTG TCC CCC GGG GAG TCA GAG CAT CTG CTG GAA CCG     984
Gly Val Asn Met Leu Ser Pro Gly Glu Ser Glu His Leu Leu Glu Pro
             220                 225                230

GCA GAA GCT GAA AGG TCT CAG AGG AGG AGG CTG CTG GTT CCA GCA AAT    1032
```

```
Ala Glu Ala Glu Arg Ser Gln Arg Arg Leu Leu Val Pro Ala Asn
235                 240                 245                 250

GAA GGT GAT CCC ACT GAG ACT CTG AGA CAG TGC TTC GAT GAC TTT GCA      1080
Glu Gly Asp Pro Thr Glu Thr Leu Arg Gln Cys Phe Asp Asp Phe Ala
                255                 260                 265

GAC TTG GTG CCC TTT GAC TCC TGG GAG CCG CTC ATG AGG AAG TTG GGC      1128
Asp Leu Val Pro Phe Asp Ser Trp Glu Pro Leu Met Arg Lys Leu Gly
                270                 275                 280

CTC ATG GAC AAT GAG ATA AAG GTG GCT AAA GCT GAG GCA GCG GGC CAC      1176
Leu Met Asp Asn Glu Ile Lys Val Ala Lys Ala Glu Ala Ala Gly His
                285                 290                 295

AGG GAC ACC TTG TAC ACG ATG CTG ATA AAG TGG GTC AAC AAA ACC GGG      1224
Arg Asp Thr Leu Tyr Thr Met Leu Ile Lys Trp Val Asn Lys Thr Gly
        300                 305                 310

CGA GAT GCC TCT GTC CAC ACC CTG CTG GAT GCC TTG GAG ACG CTG GGA      1272
Arg Asp Ala Ser Val His Thr Leu Leu Asp Ala Leu Glu Thr Leu Gly
315                 320                 325                 330

GAG AGA CTT GCC AAG CAG AAG ATT GAG GAC CAC TTG TTG AGC TCT GGA      1320
Glu Arg Leu Ala Lys Gln Lys Ile Glu Asp His Leu Leu Ser Ser Gly
                335                 340                 345

AAG TTC ATG TAT CTA GAA GGT AAT GCA GAC TCT GCC ATG TCC              1362
Lys Phe Met Tyr Leu Glu Gly Asn Ala Asp Ser Ala Met Ser
                350                 355                 360

TAAGTGTGAT TCTCTTCAGG AAGTGAGACC TTCCCTGGTT TACCTTTTTT CTGGAAAAAG    1422

CCCAACTGGA CTCCAGTCAG TAGGAAAGTG CCACAATTGT CACATGACCG GTACTGGAAG    1482

AAACTCTCCC ATCCAACATC ACCCAGTGGA TGGAACATCC TGTAACTTTT CACTGCACTT    1542

GGCATTATTT TTATAAGCTG AATGTGATAA TAAGGACACT ATGGAAAAAA AAAAAAAA     1600

(2) INFORMATION FOR SEQ ID NO:2:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Gln Arg Gly Gln Asn Ala Pro Ala Ala Ser Gly Ala Arg Lys
-51 -50                 -45                 -40

Arg His Gly Pro Gly Pro Arg Glu Ala Arg Gly Ala Arg Pro Gly Pro
-35                 -30                 -25                 -20

Arg Val Pro Lys Thr Leu Val Leu Val Val Ala Ala Val Leu Leu Leu
                -15                 -10                 -5

Val Ser Ala Glu Ser Ala Leu Ile Thr Gln Gln Asp Leu Ala Pro Gln
            1                   5                   10

Gln Arg Ala Ala Pro Gln Gln Lys Arg Ser Ser Pro Ser Glu Gly Leu
        15                  20                  25

Cys Pro Pro Gly His His Ile Ser Glu Asp Gly Arg Asp Cys Ile Ser
30                  35                  40                  45

Cys Lys Tyr Gly Gln Asp Tyr Ser Thr His Trp Asn Asp Leu Leu Phe
                50                  55                  60

Cys Leu Arg Cys Thr Arg Cys Asp Ser Gly Glu Val Glu Leu Ser Pro
            65                  70                  75

Cys Thr Thr Thr Arg Asn Thr Val Cys Gln Cys Glu Glu Gly Thr Phe
        80                  85                  90

Arg Glu Glu Asp Ser Pro Glu Met Cys Arg Lys Cys Arg Thr Gly Cys
```

```
            95                  100                 105
Pro Arg Gly Met Val Lys Val Gly Asp Cys Thr Pro Trp Ser Asp Ile
110                 115                 120                 125

Glu Cys Val His Lys Glu Ser Gly Ile Ile Ile Gly Val Thr Val Ala
                130                 135                 140

Ala Val Val Leu Ile Val Ala Val Phe Val Cys Lys Ser Leu Leu Trp
            145                 150                 155

Lys Lys Val Leu Pro Tyr Leu Lys Gly Ile Cys Ser Gly Gly Gly Gly
            160                 165                 170

Asp Pro Glu Arg Val Asp Arg Ser Ser Gln Arg Pro Gly Ala Glu Asp
            175                 180                 185

Asn Val Leu Asn Glu Ile Val Ser Ile Leu Gln Pro Thr Gln Val Pro
190                 195                 200                 205

Glu Gln Glu Met Glu Val Gln Glu Pro Ala Glu Pro Thr Gly Val Asn
                210                 215                 220

Met Leu Ser Pro Gly Glu Ser Glu His Leu Leu Glu Pro Ala Glu Ala
            225                 230                 235

Glu Arg Ser Gln Arg Arg Arg Leu Leu Val Pro Ala Asn Glu Gly Asp
            240                 245                 250

Pro Thr Glu Thr Leu Arg Gln Cys Phe Asp Asp Phe Ala Asp Leu Val
255                 260                 265

Pro Phe Asp Ser Trp Glu Pro Leu Met Arg Lys Leu Gly Leu Met Asp
270                 275                 280                 285

Asn Glu Ile Lys Val Ala Lys Ala Glu Ala Gly His Arg Asp Thr
                290                 295                 300

Leu Tyr Thr Met Leu Ile Lys Trp Val Asn Lys Thr Gly Arg Asp Ala
            305                 310                 315

Ser Val His Thr Leu Leu Asp Ala Leu Glu Thr Leu Gly Glu Arg Leu
            320                 325                 330

Ala Lys Gln Lys Ile Glu Asp His Leu Leu Ser Ser Gly Lys Phe Met
            335                 340                 345

Tyr Leu Glu Gly Asn Ala Asp Ser Ala Met Ser
350                 355                 360

(2) INFORMATION FOR SEQ ID NO:3:

(i) SEQUENCE CHARACTERISTICS:
            (A) LENGTH: 455 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:3:

Met Gly Leu Ser Thr Val Pro Asp Leu Leu Pro Leu Val Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
            50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
```

```
                85                  90                  95
Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
            130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
            210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
            290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
            450                 455

(2) INFORMATION FOR SEQ ID NO:4:

(i) SEQUENCE CHARACTERISTICS:
          (A) LENGTH: 335 amino acids
          (B) TYPE: amino acid
          (C) STRANDEDNESS: single
          (D) TOPOLOGY: linear
```

(ii) MOLECULE TYPE: protein (xi) SEQUENCE DESCRIPTION: SEQ ID NO:4:

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

(2) INFORMATION FOR SEQ ID NO:5:

(i) SEQUENCE CHARACTERISTICS:
        (A) LENGTH: 417 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

| | | | | | | | | | | | | | | |
|---|---|---|---|---|---|---|---|---|---|---|---|---|---|---|
|Met|Glu|Gln|Arg|Pro|Arg|Gly|Cys|Ala|Ala|Val|Ala|Ala|Leu|Leu|
|1| | | |5| | | |10| | | | |15| |

Leu Val Leu Leu Gly Ala Arg Ala Gln Gly Gly Thr Arg Ser Pro Arg
           20                  25                  30

Cys Asp Cys Ala Gly Asp Phe His Lys Lys Ile Gly Leu Phe Cys Cys
           35                  40                  45

Arg Gly Cys Pro Ala Gly His Tyr Leu Lys Ala Pro Cys Thr Glu Pro
     50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
           100                 105                 110

Thr Arg Cys Gly Cys Lys Pro Gly Trp Phe Val Glu Cys Gln Val Ser
           115                 120                 125

Gln Cys Val Ser Ser Ser Pro Phe Tyr Cys Gln Pro Cys Leu Asp Cys
     130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
           180                 185                 190

Ala Val Cys Gly Trp Arg Gln Met Phe Trp Val Gln Val Leu Leu Ala
     195                 200                 205

Gly Leu Val Val Pro Leu Leu Leu Gly Ala Thr Leu Thr Tyr Thr Tyr
210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
           260                 265                 270

Thr Val Gln Leu Val Gly Asn Ser Trp Thr Pro Gly Tyr Pro Glu Thr
     275                 280                 285

Gln Glu Ala Leu Cys Pro Gln Val Thr Trp Ser Trp Asp Gln Leu Pro
     290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
           340                 345                 350

Thr Leu Gly Leu Arg Glu Ala Glu Ile Glu Ala Val Glu Val Glu Ile
           355                 360                 365

Gly Arg Phe Arg Asp Gln Gln Tyr Glu Met Leu Lys Arg Trp Arg Gln
     370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro (2) INFORMATION FOR SEQ ID NO:6:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AATTCGGCAC AGCTCTTCAG GAAGTCAGAC CTTCCCTGGT TTACCTTTTT TCTGGAAAAA    60
GCCCAACTGG GACTCCAGTC AGTAGGAAAG TGCCACAATT GTCACATGAC CGGTACTGGA   120
AGAAACTCTC CCATCCAACA TCACCCAGTG GNATGGGAAC ACTGATGAAC TTTTCACTGC   180
ACTTGGCATT ATTTTTGTNA AGCTGAATGT GATAATAAGG GCACTGATGG AAATGTCTGG   240
ATCATTCCGG TTGTGCGTAC TTTGAGATTT GNGTTTGGGG ATGTNCATTG TGTTTGACAG   300
CACTTTTTTN ATCCCTAATG TNAAATGCNT NATTTGATTG TGANTTGGGG GTNAACATTG   360
GTNAAGGNTN CCCNTNTGAC ACAGTAGNTG GTNCCCGACT TANAATNGNN GAANANGATG   420
NATNANGAAC CTTTTTTTGG GTGGGGGGGT NNCGGGGCAG TNNAAGNGNG NCTCCCCAGG   480
TTTGGNGTNG CAATNGNGGA ANNNTGG                                      507
```

(2) INFORMATION FOR SEQ ID NO:7:

(i) SEQUENCE CHARACTERISTICS:
        (A) LENGTH: 226 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TTTTTTTTGT AGATGGATCT TACAATGTAG CCCAAATAAA TAAATAAAGC ATTTACATTA    60
GGATAAAAAA GTGCTGTGAA AACAATGACA TCCCAAACCA AATCTCAAAG TACGCACAAA   120
CGGAATGATC CAGACATTTC CATAGGTCCT TATTATCACA TTCAGCTTAT AAAATAATGC   180
CAAGTGCAGT GAAAAGTTAC AGGATGTTCC ATCCACTGGG TGGATT                  226
```

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CGCCCATGGA GTCTGCTCTG ATCAC                                          25
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:9:

CGCAAGCTTT TAGCCTGATT CTTTGTGGAC                30

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCGGATCCG CCATCATGGA ACAACGGGGA CAGAAC         36

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCGGTACCT TAGGACATGG CAGAGTC                   27

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCGGTACCT TAGCCTGATT CTTTGTGGAC                30